US011311725B2

(12) United States Patent
Levine et al.

(10) Patent No.: US 11,311,725 B2
(45) Date of Patent: Apr. 26, 2022

(54) SYSTEMS AND METHODS FOR STIMULATING AND/OR MONITORING LOCI IN THE BRAIN TO TREAT INFLAMMATION AND TO ENHANCE VAGUS NERVE STIMULATION

(71) Applicant: SetPoint Medical Corporation, Valencia, CA (US)

(72) Inventors: Jacob A. Levine, West Hempstead, NY (US); Michael A. Faltys, Valencia, CA (US)

(73) Assignee: SetPoint Medical Corporation, Valencia, CA (US)

( * ) Notice: Subject to any disclaimer, the term of this patent is extended or adjusted under 35 U.S.C. 154(b) by 58 days.

(21) Appl. No.: 14/922,022

(22) Filed: Oct. 23, 2015

(65) Prior Publication Data

US 2016/0114165 A1 Apr. 28, 2016

Related U.S. Application Data

(60) Provisional application No. 62/068,473, filed on Oct. 24, 2014.

(51) Int. Cl.
*A61N 1/36* (2006.01)
*A61N 1/05* (2006.01)
(Continued)

(52) U.S. Cl.
CPC ............ *A61N 1/3606* (2013.01); *A61B 5/369* (2021.01); *A61N 1/0526* (2013.01); *A61N 1/0529* (2013.01); *A61N 1/0551* (2013.01); *A61N 1/36053* (2013.01); *A61N 1/36125* (2013.01); *A61N 1/36135* (2013.01); *A61N 1/36139* (2013.01); *A61N 1/36146* (2013.01);
(Continued)

(58) Field of Classification Search
None
See application file for complete search history.

(56) References Cited

U.S. PATENT DOCUMENTS

| 2,164,121 A | 6/1939 | Pescador |
| 3,363,623 A | 1/1968 | Atwell |

(Continued)

FOREIGN PATENT DOCUMENTS

| CN | 201230913 | 5/2009 |
| CN | 101528303 A | 9/2009 |

(Continued)

OTHER PUBLICATIONS

US 6,184,239 B1, 02/2001, Puskas (withdrawn)
(Continued)

*Primary Examiner* — Kaylee R Wilson
*Assistant Examiner* — Jay B Shah
(74) *Attorney, Agent, or Firm* — Shay Glenn LLP

(57) ABSTRACT

Described herein are methods and systems for using EEG recordings to improve vagus nerve stimulation (VNS) therapy. In particular, described herein are methods and systems for using EEG recordings to detect P300 and/or activation of the nucleus basalis and/or the locus coeruleus to determine the efficacy of VNS. The EEG recordings can be used to provide feedback control to help optimize stimulation parameters and to screen for patients that respond well to VNS therapy.

14 Claims, 16 Drawing Sheets

(51) Int. Cl.

| | | |
|---|---|---|
| *A61N 2/00* | (2006.01) | |
| *A61N 1/372* | (2006.01) | |
| *A61N 1/375* | (2006.01) | |
| *A61B 5/369* | (2021.01) | |
| *A61N 2/02* | (2006.01) | |
| *A61B 5/00* | (2006.01) | |
| *A61N 1/378* | (2006.01) | |
| *A61B 5/377* | (2021.01) | |

(52) U.S. Cl.
CPC ....... *A61N 1/3756* (2013.01); *A61N 1/37205* (2013.01); *A61N 2/006* (2013.01); *A61B 5/377* (2021.01); *A61B 5/4041* (2013.01); *A61B 5/4064* (2013.01); *A61N 1/0534* (2013.01); *A61N 1/0556* (2013.01); *A61N 1/3758* (2013.01); *A61N 1/3787* (2013.01); *A61N 1/37247* (2013.01); *A61N 2/02* (2013.01)

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kern et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |

(56) References Cited

U.S. PATENT DOCUMENTS

| | | |
|---|---|---|
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hili et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 * | 11/2008 | Armstrong ......... A61N 1/36135 600/301 |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |

(56) References Cited

U.S. PATENT DOCUMENTS

| | | |
|---|---|---|
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1* | 2/2005 | Devlin ............... A61B 5/048 607/45 |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |

(56) References Cited

U.S. PATENT DOCUMENTS

| | | |
|---|---|---|
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1* | 2/2008 | Dietrich ............... A61H 39/002 607/45 |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234790 A1 | 9/2008 | Bayer et al. |
| 2008/0249439 A1 | 10/2008 | Tracey et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125079 A1 | 5/2009 | Armstrong et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0241207 A1 | 9/2010 | Bluger |
| 2010/0249859 A1 | 9/2010 | DiLorenzo |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0190849 A1* | 8/2011 | Faltys ............... A61N 1/36053 607/50 |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2013/0013016 A1 | 1/2013 | Diebold |

(56) References Cited

U.S. PATENT DOCUMENTS

| | | | |
|---|---|---|---|
| 2013/0066392 A1* | 3/2013 | Simon | A61N 2/006 607/45 |
| 2013/0066395 A1 | 3/2013 | Simon et al. | |
| 2013/0079834 A1 | 3/2013 | Levine | |
| 2013/0245718 A1 | 9/2013 | Birkholz et al. | |
| 2013/0253413 A1 | 9/2013 | Levine et al. | |
| 2013/0317580 A1 | 11/2013 | Simon et al. | |
| 2014/0046407 A1 | 2/2014 | Ben-Ezra et al. | |
| 2014/0206945 A1 | 7/2014 | Liao | |
| 2014/0257425 A1 | 9/2014 | Arcot-Krishnamurthy et al. | |
| 2014/0288551 A1 | 9/2014 | Bharmi et al. | |
| 2014/0330335 A1 | 11/2014 | Errico et al. | |
| 2015/0018728 A1 | 1/2015 | Gross et al. | |
| 2015/0100100 A1 | 4/2015 | Tracey et al. | |
| 2015/0119956 A1 | 4/2015 | Libbus et al. | |
| 2015/0233904 A1 | 8/2015 | Nayak | |
| 2015/0241447 A1 | 8/2015 | Zitnik et al. | |
| 2016/0051813 A1 | 2/2016 | Faltys et al. | |
| 2016/0096016 A1 | 4/2016 | Tracey et al. | |
| 2016/0096017 A1 | 4/2016 | Levine et al. | |
| 2016/0367808 A9 | 12/2016 | Simon et al. | |
| 2017/0304613 A1 | 10/2017 | Faltys et al. | |
| 2018/0001096 A1 | 1/2018 | Faltys et al. | |
| 2018/0021217 A1 | 1/2018 | Tracey et al. | |
| 2018/0021580 A1 | 1/2018 | Tracey et al. | |
| 2018/0117320 A1 | 5/2018 | Levine et al. | |
| 2018/0289970 A1 | 10/2018 | Faltys et al. | |
| 2019/0046799 A1 | 2/2019 | Levine et al. | |
| 2019/0111263 A1 | 4/2019 | Levine et al. | |
| 2019/0117979 A1 | 4/2019 | Tracey et al. | |
| 2019/0192847 A1 | 6/2019 | Faltys et al. | |
| 2019/0275328 A1 | 9/2019 | Zitnik et al. | |
| 2020/0330760 A1 | 10/2020 | Levine et al. | |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 | 2/1910 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO2003/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |

OTHER PUBLICATIONS

Pongratz et al. (The sympathetic nervous response in inflammation; Arthritis Research & Therapy 2014, 16:504).*

Manta et al. (Optimization of vagus nerve stimulation parameters using the firing activity of serotonin neurons in the rat dorsal raphe; European Neuropsychopharmacology (2009) 19, 250-255 ).*

Cavaillon et al.; The pro-inflammatory cytokine casade; Immune Response in the Critically Ill; Springer-Verlag Berlin Hiedelberg; pp. 37-66; Jan. 21, 2002.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Anderson et al.; Reflex principles of immunological homeostasis; Annu. Rev. Immunol.; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression IN shock, New York Surgical Society, New York, NY, Apr. 11, 2001.

Bernik, et al.. Pharmacological stimulation of the cholinergic antiinflammatory pathway, The Journal of Experimental Medicine, vol. 195, No. 6, pp. 781-788, Mar. 18, 2002.

Besedovsky, H., et al., Immunoregulatory feedback between interleukin-1 and glucocorticoid hormones, Science, vol. 233, No. 4764, pp. 652-654, Aug. 1986.

Bhattacharya, S.K. et al., Central muscarinic receptor subtypes and carrageenin-induced paw oedema in rats, Res. Esp. Med. vol. 191(1), pp. 65-76, Dec. 1991.

Bianchi et al., Suppression of proinflammatory cytokines in monocytes by a tetravalent guanylhydrazone, Journal of Experimental Medicine, vol. 183, pp. 927-936, Mar. 1996.

Biggio et al.; Chronic vagus nerve stimulation induces neuronal plasticity in the rat hippocampus; Int. J. Neurpsychopharmacol.; vol. 12; No. 9; pp. 1209-1221; Oct. 2009.

Blackwell, T. S. et al., Sepsis and cytokines: current status, Br. J. Anaesth., vol. 77(1), pp. 110-117, Jul. 1996.

Blum, A. et al., Role of cytokines in heart failure, Am. Heart J., vol. 135(2), pp. 181-186, Feb. 1998.

Boldyreff, Gastric and intestinal mucus, its properties and physiological importance, Acta Medica Scandinavica (journal), vol. 89, Issue 1-2, pp. 1-14, Jan./Dec. 1936.

Borovikova et al., Acetylcholine inhibition of immune response to bacterial endotoxin in human macrophages, Abstracts, Society for Neuroscience, 29th Annual Meeting, Miami Beach, FL, Oct. 23-28, 1999, Abstract No. 624.6.

Borovikova et al., Efferent vagus nerve activity attenuates cytokine-mediated inflammation, Society for Neuroscience Abstracts, vol. 26, No. 102, Nov. 4-9, 2000 (abstract only).

(56) References Cited

OTHER PUBLICATIONS

Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve In the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785; pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, pp. 189-204, (year of pub. Sufficiently earlier than effective US filing date and any foreign priority date) 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.
Cheyuo et al.; The parasympathetic nervous system in the quest for stroke therapeutics; J. Cereb. Blood Flow Metab.; 31(5); pp. 1187-1195; May 2011.
Cicala et al., "Linkage between inflammation and coagulation: An update on the molecular basis of the crosstalk," Life Sciences, vol. 62(20); pp. 1817-1824, Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroImmunoModulation, vol. 12(5), pp. 307-309, Sep. 2005.
Dake; Chronic cerebrospinal venous insufficiency and multiple sclerosis: Hostory and background; Techniques Vasc. Intervent. Radiol.; 15(2); pp. 94-100; Jun. 2012.
Das, Critical advances in spticemia and septic shock, Critical Care, vol. 4, pp. 290-296, Sep. 7, 2000.
Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Diamond et al.; Mapping the immunological homunculus; Proc. Natl. Acad. Sci. USA; 108(9); pp. 3461-3462; Mar. 1, 2011.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, FASEB J., vol. 8, No. 15, pp. 1314-1325, Dec. 1994.
Dorr et al.; Effect of vagus nerve stimulation on serotonergic and noradrenergic transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Ellington et al., In vitro selection of RNA molecules that bind specific ligands, Nature, vol. 346, pp. 818-822, Aug. 30, 1990.
Ellrich et al.; Transcutaneous vagus nerve stimulation; Eur. Neurological Rev.; 6(4); pp. 254-256; 2011 (year of pub. sufficiently earlier than effective US filing date and any foreign priority date).
Engineer et al.; Directing neural plasticity to understand and treat tinnitus; Hear. Res.; 295; pp. 58-66; Jan. 2013.
Engineer et al.; Reversing pathological neural activity using targeted plasticity; Nature; 470(7332); pp. 101-104; Feb. 3, 2011 (Author Manuscript).
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.
Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gao et al.; Investigation of specificity of auricular acupuncture points in regulation of autonomic function in anesthetized rats; Autonomic Neurosc.; 138(1-2); pp. 50-56; Feb. 29, 2008.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(−)-ET 126: A potent and selective M1 antagonist in vitro and in vivo, Life Sciences, vol. 58, No. 12, pp. 991-1000, Feb. 1996.
Ghia, et al., The vagus nerve: a tonic inhibitory influence associated with inflammatory bowel disease in a murine model, Gastroenterology, vol. 131, No. 4, pp. 1122-1130, Oct. 2006.
Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, Apr. 2007.
Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.

(56) References Cited

OTHER PUBLICATIONS

Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Groves et al.; Recordings from the rat locus coeruleus during acute vagal nerve stimulation in the anaesthetised rat; Neuroscience Letters; 379(3); pp. 174-179; May 13, 2005.
Guarente, Leonard, Ph. D.; Sirtuins, Aging, and Medicine; N Engl J Med ; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; p. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; (year of pub. sufficiently earlier than effective US filing date and any foreign priority date) 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monocuclear cells in children with chronic hepatitis B virus infection, J. Pediatr. Gastroenterol., vol. 29, No. 5, pp. 540-545, Nov. 1999.
Hu, et al., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.
Ilton et al., "Differential expression of neutrophil adhesion molecules during coronary artery surgery with cardiopulmonary bypass" Journal of Thoracic and Cardiovascular Surgery, Mosby—Year Book, inc., St. Louis, Mo, US, pp. 930-937, Nov. 1, 1999.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.
Joshi et al., Potent inhibition of human immunodeficiency virus type 1 replection by template analog reverse transcriptase , J. Virol., 76(13), pp. 6545-6557, Jul. 2002.

Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kalishevskaya et al. "The character of vagotomy-and atropininduced hypercoagulation," Sechenov Physiological Journal of the USSR, 65(3): pp. 398-404, Mar. 1979.
Kalishevskaya et al.; Nervous regulation of the fluid state of the blood; Usp. Fiziol. Nauk;,vol. 13; No. 2; pp. 93-122; Apr.-Jun. 1982.
Kanai, T. et al., Interleukin-18 and Crohn's disease, Digestion, vol. 63, suppl. 1, pp. 37-42, (year of pub. sufficiently earlier than effective US filing date and any foreign priority date) 2001.
Katagiri, M., et al., Increased cytokine production by gastric mucosa in patients with helicobacter pylori infection, J. Clin, Gastroenterol., vol. 25, Suppl. 1, pp. S211-S214, (year of pub. sufficiently earlier than effective US filing date and any foreign priority date) 1997.
Kawashima, et al., Extraneuronal cholinergic system in lymphocytes, Pharmacology & Therapeutics, vol. 86, pp. 29-48, Apr. 2000.
Kees et al.; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), p. 18271-18278, Jun. 16, 2000.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep. 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.
Krarup et al.; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxininduced peak circulating level of tumor necrosis factor in rats, Shock, vol. 5, No. 5, pp. 385-388, May 1996.
Kuznik, "Role of the vascular wall in the process of hemostatis," Usp Sovrem Biol., vol. 75(1): pp. 61-85, (year of pub. sufficiently earlier than effective US filing date and any foreign priority date) 1973.
Kuznik, et al., "Blood Coagulation in stimulation of the vagus nerve in cats," Biull. Eskp. Biol. Med., vol. 78(7): pp. 7-9, (year of pub. sufficiently earlier than effective US filing date and any foreign priority date) 1974.
Kuznik, et al., "Heart as an efferent regulator of the process of blood coagulation and fibrinolysis," Kardiologiia, vol. 13(3): pp. 10-17, (year of pub. sufficiently earlier than effective US filing date and any foreign priority date) 1973.
Kuznik, et al., "Role of the heart and vessels in regulating blood coagulation and fibrinolysis," Kagdiologiia, vol. 13(4): pp. 145-154, (year of pub. sufficiently earlier than effective US filing date and any foreign priority date) 1973.
Kuznik, et al., "Secretion of blood coagulation factors into saliva under conditions of hypo-and hypercoagulation," Voprosy Meditsinskoi Khimii, vol. 19(1): pp. 54-57; (year of pub. sufficiently earlier than effective US filing date and any foreign priority date) 1973.

(56) References Cited

OTHER PUBLICATIONS

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filing date and any foreign priority date) 1975.
Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
LeNovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; (year of pub. sufficiently earlier than effective US filing date and any foreign priority date) 2006.
Lipton, J. M. et al.; Anti-inflammatory actions of the neuroimmunomodulator ?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Martindale: The Extra Pharmacopoeia; 28th Ed. London; The pharmaceutical press; pp. 446-485; (year of pub. sufficiently earlier than effective US filing date and any foreign priority date) 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, (year of pub. sufficiently earlier than effective US filing date and any foreign priority date) 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; (year of pub. sufficiently earlier than effective US filing date and any foreign priority date) 2004.
Mishchenko, et al., "Coagulation of the blood and fibrinolysos in dogs during vagal stimulation," Sechenov Physiological Journal of the USSR, vol. 61(1): pp. 101-107, (year of pub. sufficiently earlier than effective US filing date and any foreign priority date) 1975.
Mishchenko, "The role of specific adreno-and choline-receptors of the vascular wall in the regulation of blood coagulation in the stimulation of the vagus nerve," Biull. Eskp. Biol. Med., vol. 78(8); pp. 19-22, (year of pub. sufficiently earlier than effective US filing date and any foreign priority date) 1974.
Molina et al., CNI-1493 attenuates hemodynamic and pro-inflammatory responses to LPS, Shock, vol. 10, No. 5, pp. 329-334, Nov. 1998.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79 (2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering Online, 2(1), pp. 6, Mar. 4, 2003.
Olofsson et al.; Rethinking inflammation: neural circuits in the regulation of immunity; Immunological Reviews; 248(1); pp. 188-204; Jul. 2012.
Oshinsky et al.; Non-invasive vagus nerve stimulation as treatment for trigeminal allodynia; Pain; 155(5); pp. 1037-1042; May 2014.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Pateyuk, et al.."Treatment of Botkin's disease with heparin," Klin. Med., vol. 51(3): pp. 113-117, Mar. 1973.
Pavlov et al; Controlling inflammation: the cholinergic anti-inflammatory pathway; Biochem. Soc. Trans.; 34(Pt 6); pp. 1037-1040; Dec. 2006.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-815, Mar. 24, 1994.
Pulvirenti et al; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiograph on the Action of the Vagus Nerve on the Human Heart; J Exp Med; 14(3):217-234; Sep. 1911.
Romanovsky, A. A., et al.,The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.

(56) References Cited

OTHER PUBLICATIONS

Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear ieukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, (year of pub. sufficiently earlier than effective US filing date and any foreign priority date) 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.
Sokratov, et al. "The role of choline and adrenegic structures in regulation of renal excretion of hemocoagulating compounds into the urine," Sechenov Physiological Journal of the USSR, vol. 63(12): pp. 1728-1732, (year of pub. sufficiently earlier than effective US filing date and any foreign priority date) 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95, pp. 31-35, (year of pub. sufficiently earlier than effective US filing date and any foreign priority date) 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; (year of pub. sufficiently earlier than effective US filing date and any foreign priority date) 1969.
Strojnik et al.; Treatment of drop foot using and implantable peroneal underknee stimulator; Scand. J. Rehab. Med.; vol. 19(1); p. 37R43; (year of pub. sufficiently earlier than effective US filing date and any foreign priority date) 1987.
Sugano et al., Nicotine inhibits the production of inflammatory mediators in U937 cells through modulation of nuclear factor-kappaß activation, Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; 1994 (year of pub. sufficiently earlier than effective US filing date and any foreign priority date).
Sykes, et al., An investigation into the effect and mechanisms of action of nicotine in inflammatory bowel disease, Inflamm. Res., vol. 49, pp. 311-319, Jul. 2000.
Takeuchi et al., A comparision between Chinese blended medicine "Shoseiryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J.; Reflex control of immunity; Nat Rev Immunol; 9(6); pp. 418-428; Jun. 2009.
Tracey, K. J. et al., Shock and tissue injury induced by recombinant human cachectin, Science, vol. 234, pp. 470-474, Oct. 24, 1986.
Tracey, K.J., The inflammatory reflex, Nature, vol. 420, pp. 853-859, Dec. 19-26, 2002.
Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Van Der Horst et al.; Stressing the role of FoxO proteins in lifespan and disease; Nat Rev Mol Cell Biol.; vol. 8; No. 6; pp. 440-450; Jun. 2007.
Vanhoutte, et al., Muscarinic and beta-adrenergic prejunctional modulation of adrenergic neurotransmission in the blood vessel wall, Gen Pharmac., vol. 14, pp. 35-37, (year of pub. sufficiently earlier than effective US filing date and any foreign priority date) 1983.
VanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16 (2), pp. 101-102, (year of pub. sufficiently earlier than effective US filing date and any foreign priority date) 2000.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?/-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.

(56) References Cited

OTHER PUBLICATIONS

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al.. Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetylase SIRT1.; Science; Vo. 323; No. 5717; pp. 1063-1066; Feb. 2009.
Whaley, K. et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yeh, S.S. et al., Geriatric cachexia: the role of cytokines, Am. J. Clin. Nutr., vol. 70(2), pp. 183-197, Aug. 1999.
Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.
Zamotrinsky et al.; Vagal neurostimulation in patients with coronary artery disease; Auton. Neurosci.; 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.
Zhang et al.; Roles of SIRT1 in the acute and restorative phases following induction of inflammation.; J Biol Chem.; vol. 285; No. 53; pp. 41391-41401; Dec. 2010.
Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.
Zhao et al.; Transcutaneous auricular vagus stimulation protects endotoxemic rat from lipopolysaccharide-induced inflammation; Evid. Based Complement Alternat. Med.; vol. 2012; Article ID 627023; 10 pages; Dec. 29, 2012.
Levine et al.; U.S. Appl. No. 14/782,715 entitled "Closed-loop vagus nerve stimulation," filed Oct. 6, 2015.
Faltys et al.; U.S. Appl. No. 14/887,192 entitled "Neural stimulation devices and systems for treatment of chronic inflammation," filed Oct. 19, 2015.
Levine et al.; U.S. Appl. No. 15/398,615 entitled "Devices and methods for modulation of bone erosion," filed Jan. 4, 2017.
Faltys et al.; U.S. Appl. No. 15/406,619 entitled "Systems and methods for establishing a nerve block," filed Jan. 13, 2017.
Levine et al.; U.S. Appl. No. 15/411,933 entitled "Control of vagal stimulation," filed Jan. 20, 2017.
Zitnik et al.; U.S. Appl. No. 15/411,936 entitled "Implantable microstimulators and inductive charging systems," filed Jan. 20, 2017.
Faltys et al.; U.S. Appl. No. 15/415,764 entitled "Implantable neurostimulator having power control and thermal regulation and methods of use," filed Jan. 25, 2017.
Faltys et al.; U.S. Appl. No. 15/153,639 entitled "External programmer," filed May 12, 2016.
Tracey et al.; U.S. Appl. No. 15/616,855 entitled "Inhibition of inflammatory cytokine production by cholinergic agonists and vagus nerve stimulation," filed Jun. 7, 2017.
Faltys et al.; U.S. Appl. No. 16/544,805 entitled "Nerve cuff with pocket for leadless stimulator," filed Aug. 19, 2019.
Faltys et al.; U.S. Appl. No. 16/544,882 entitled "Neural stimulation devices and systems for treatment of chronic inflammation," filed Aug. 19, 2019.
Crusz et al.; Inflammation and cancer; advances and new agents; Nature reviews Clinical Oncology; 12(10); pp. 584-596; doi: 10.1038/nrclinonc.2015.105; Jun. 30, 2015.
Strowig et al.; Inflammasomes in health and disease; Nature; vol. 481; pp. 278-286; doi: 10.1038/nature10759; Jan. 19, 2012.
Manogue; U.S. Appl. No. 16/582,726 entitled "Methods and apparatuses for reducing bleeding via coordinated trigeminal and vagal nerve stimulation," filed Sep. 25, 2019.
Katsavos et al.; Biomarkers in multiple sclerosis: an up-to-date overview; Multiple Sclerosis International; vol. 2013, Article ID 340508, 20 pages; (year of pub. sufficiently earlier than effective US filing date and any foreign priority date) 2013.
Faltys et al.; U.S. Appl. No. 16/728,880 entitled "Implantable neurostimulator having power control and thermal regulation and methods of use," filed Dec. 27, 2019.
Faltys et al.; U.S. Appl. No. 16/785,400 entitled "Systems and methods for establishing a nerve block," filed Feb. 7, 2020.
Levine et al.; U.S. Appl. No. 17/337,292 entitled "Closed-loop vagus nerve stimulation," filed Jun. 2, 2021.
Palov et al.; The cholinergic anti-inflammatory pathway: a missing link in neuroimmunomodulation; Molecular Medicine; 9(5); pp. 125-134; May 2003.
Tracey et al.; U.S. Appl. No. 17/170,772 entitled "Treatment of bleeding by non-invasive stimulation," filed Feb. 8, 2021.
Koopman et al., Pilot study of stimulation of the cholinergic anti-infammatory pathway with an implantable vagus nerve stimulation device in patients with rheumatoid arthritis; 2012 ACR/ARHP Annual Meeting; Abstract No. 451; 4 pages; retrieved from the internet (https://acrabstracts.org/abstfact/pilot-study-of-stimuiation-of-the-cholinergic-anti-inflammatory-pathway-with-an-impiantable-vagus-nerve-stimulation-device-in-patients-with-rheumatoid-arthritis); (Abstract Only); on Sep. 24, 2020.
Pavlov et al.; The cholinergic anti-inflammatory pathway; Brain, Behavior, and Immunity; 19; p. 493-499; Nov. 2005.
Zitnik et al.; Treatment of chronic inflammatory diseases with implantable medical devices; Cleveland Clinic Journal of Medicine; 78(Suppl 1); pp. S30-S34; Aug. 2011.
Koopman et al.; THU0237 first-in-human study of vagus nerve stimulation for rheumatoid arthritis: clinical and biomarker results through day 84; Annals of the Rheumatic Diseases; 72(Suppl 3):A245; Jun. 1, 2013 (Abstract Only).
Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.
Mayo Clinic; The factsheet of vagus nerve stimulation from the Mayo Clinic website: www.mayoclinic.org/tests-procedures/vagus-nerve-stimulation/about/pac-20384565; retrieved from the internet on Sep. 28, 2021.

\* cited by examiner

107
Prescription Pad

105
Energizer (Patient Charger)

103
Microstimulator + Pod

101

SYSTEMS AND METHODS FOR STIMULATING AND/OR MONITORING LOCI IN THE BRAIN TO TREAT INFLAMMATION AND TO ENHANCE VAGUS NERVE STIMULATION

CROSS REFERENCE TO RELATED APPLICATIONS

This patent application claims priority to U.S. Provisional Patent Application No. 62/068,473, titled "EXTREMELY LOW DUTY-CYCLE ACTIVATION OF THE CHOLINERGIC ANTI-INFLAMMATORY PATHWAY, AND TRAINING THEREOF, TO TREAT CHRONIC INFLAMMATION," filed Oct. 24, 2014, which is herein incorporated by reference in its entirety.

Some variations of the methods and apparatuses described in this patent application may be related to the following U.S. patent applications: U.S. patent application Ser. No. 12/620,413, filed on Nov. 17, 2009 and titled, "DEVICES AND METHODS FOR OPTIMIZING ELECTRODE PLACEMENT FOR ANTI-INFLAMATORY STIMULATION" (US-2010-0125304); U.S. patent application Ser. No. 12/874,171, filed on Sep. 1, 2010 and titled, "PRESCRIPTION PAD FOR TREATMENT OF INFLAMMATORY DISORDERS" (US-2011-0054569); U.S. patent application Ser. No. 12/917,197, filed on Nov. 1, 2010 and titled, "MODULATION OF THE CHOLINERGIC ANTI-INFLAMMATORY PATHWAY TO TREAT PAIN OR ADDICTION" (US-2011-0106208); U.S. patent application Ser. No. 12/978,250, filed on Dec. 23, 2010 and titled, "NEURAL STIMULATION DEVICES AND SYSTEMS FOR TREATMENT OF CHRONIC INFLAMMATION" (US-2011-0190849); U.S. patent application Ser. No. 12/797,452, filed on Jun. 9, 2010 and titled, "NERVE CUFF WITH POCKET FOR LEADLESS STIMULATOR" (US-2010-0312320); U.S. patent application Ser. No. 13/467,928, filed on May 9, 2012 and titled, "SINGLE-PULSE ACTIVATION OF THE CHOLINERGIC ANTI-INFLAMMATORY PATHWAY TO TREAT CHRONIC INFLAMMATION" (US-2012-0290035); and U.S. patent application Ser. No. 13/338,185, filed on Dec. 27, 2011 and titled, "MODULATION OF SIRTUINS BY VAGUS NERVE STIMULATION." Each of these patent applications is herein incorporated by reference in its entirety.

Some variations of the methods and apparatuses described in this patent application may be related to the following PCT application: International Application No. PCT/US2014/033690, filed Apr. 10, 2014, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

For example, the following reference are incorporated by reference herein in their entireties:

1. Cheyuo, C., et al., The parasympathetic nervous system in the quest for stroke therapeutics. J Cereb Blood Flow Metab, 2011. 31(5): p. 1187-95.
2. Engineer, N. D., A. R. Moller, and M. P. Kilgard, Directing neural plasticity to understand and treat tinnitus. Hear Res, 2013. 295: p. 58-66.
3. Groves, D. A., E. M. Bowman, and V. J. Brown, Recordings from the rat locus coeruleus during acute vagal nerve stimulation in the anaesthetised rat. Neuroscience Letters, 2005. 379(3): p. 174-179.
4. Don, A. E. and G. Debonnel, Effect of vagus nerve stimulation on serotonergic and noradrenergic transmission. J Pharmacol Exp Ther, 2006. 318(2): p. 890-8.
5. Clark, K. B., et al., Enhanced recognition memory following vagus nerve stimulation in human subjects. Nat Neurosci, 1999. 2(1): p. 94-8.
6. Engineer, N. D., et al., Reversing pathological neural activity using targeted plasticity. Nature, 2011. 470 (7332): p. 101-4.
7. Diamond, B. and K. J. Tracey, Mapping the immunological homunculus. Proc Natl Acad Sci USA, 2011. 108(9): p. 3461-2.
8. Swick, D., et al., Locus coeruleus neuronal activity in awake monkeys: relationship to auditory P300-like potentials and spontaneous EEG. Experimental Brain Research, 1994. 101(1): p. 86-92.
9. Neuhaus, A. H., et al., P300 is enhanced in responders to vagus nerve stimulation for treatment of major depressive disorder. J Affect Disord, 2007. 100(1-3): p. 123-8.

FIELD

Embodiments of the invention relate generally to neuromodulation of the vagus nerve for the treatment of inflammation, and more specifically to neuromodulation of the vagus nerve involving feedback and/or stimulation from the central nervous system.

BACKGROUND

Some neuromodulation devices have the ability to modulate their own stimulation settings quickly based on immediate feedback from target tissue (e.g. muscle) that they are stimulating, since the target tissue responds quickly to stimulation. For example, electromyography (EMG) can be used to record and evaluate the electrical activity of muscles, which provides information regarding the activation level and/or recruitment of the muscles. This information can be processed and used to modulate the neurostimulation parameters applied to the muscles, thereby improving the efficacy of the stimulation device.

Vagus nerve stimulation (VNS) for the treatment of chronic inflammatory diseases, on the other hand, is not easily programmed for optimal result, as decreases in inflammation take hours to days to manifest. Consequently, it would be desirable to identify alternative markers or surrogates that indicate activation of the cholinergic anti-inflammatory pathway by VNS. In addition, it would be desirable to use these alternative markers or surrogates to identify patients that may be suitable for receiving VNS therapy. Furthermore, it would be desirable to directly modulate these markers or surrogates as an alternative or supplemental way to treat inflammation.

SUMMARY OF THE DISCLOSURE

The present invention relates generally to neuromodulation of the vagus nerve for the treatment of inflammation, and more specifically to neuromodulation of the vagus nerve involving feedback and/or stimulation from the central nervous system.

In some embodiments, a method for inducing long term potentiation of the inflammatory reflex in a patient is provided. The method can include stimulating the vagus nerve of the patient according to a set of stimulation parameters; recording an EEG after the step of stimulating the vagus nerve; determining from the recorded EEG whether at least one of the nucleus basalis and the locus coeruleus has been activated by the vagus nerve stimulation; and adjusting the set of stimulation parameters based on the determination from the recorded EEG whether at least one of the nucleus basalis and the locus coeruleus has been activated.

In some embodiments, the step of adjusting the set of stimulation parameters includes increasing a stimulation amplitude.

In some embodiments, the method further includes recording a baseline EEG.

In some embodiments, the step of determining from the recorded EEG whether at least one of the nucleus basalis and the locus coeruleus has been activated by the vagus nerve stimulation comprises comparing the recorded EEG with the baseline EEG.

In some embodiments, a method for inducing long term potentiation of the inflammatory reflex in a patient is provided. The method can include stimulating the vagus nerve according to a set of stimulation parameters sufficient for activating at least one of the nucleus basalis and the locus coeruleus.

In some embodiments, the set of stimulation parameters includes an amplitude between about 0.1 and 3 mA, a frequency between about 1 Hz and 30 Hz, a pulse width between about 100 uS and 500 uS, and a duration between about 0.5 second to 10 minutes.

In some embodiments, a method for prescreening a patient is provided. The method can include noninvasively stimulating the vagus nerve; recording an EEG; and determining whether the patient will be responsive to an invasive vagus nerve stimulation based on an analysis of the EEG.

In some embodiments, the step of determining whether the patient will be responsive to an invasive vagus nerve stimulation based on an analysis of the EEG includes determining whether P300 is present in the EEG.

In some embodiments, the step of determining whether the patient will be responsive to an invasive vagus nerve stimulation based on an analysis of the EEG includes determining with the EEG whether at least one of the nucleus basalis and the locus coeruleus was activated by the noninvasive vagus nerve stimulation.

In some embodiments, the step of noninvasively stimulating the vagus nerve includes noninvasively stimulating the auricular branch of the vagus nerve.

In some embodiments, the noninvasive stimulation of the auricular branch of the vagus nerve is electrical.

In some embodiments, the noninvasive stimulation of the auricular branch of the vagus nerve is mechanical.

In some embodiments, the step of recording the ECG takes place after the step of noninvasively stimulating the vagus nerve.

In some embodiments, the step of recording the ECG takes place during the step of noninvasively stimulating the vagus nerve.

In some embodiments, a method for providing feedback control during vagus nerve stimulation of a patient is provided. The method can include stimulating the vagus nerve with a vagus nerve stimulator; recording an EEG to detect at least one of P300, activation of the nucleus basalis, and activation of the locus coeruleus; and adjusting an amplitude of the stimulation to the vagus nerve until at least one of P300, activation of the nucleus basalis, and activation of the locus coeruleus is detected in the EEG.

In some embodiments, the method further includes programming the vagus nerve stimulator with a set of stimulation parameters based on the step of adjusting the amplitude of the stimulation to the vagus nerve until at least one of P300, activation of the nucleus basilis, and activation of the locus coeruleus is detected in the EEG.

In some embodiments, the step of adjusting the amplitude includes increasing the amplitude when the patient is not responding to the stimulation of the vagus nerve.

In some embodiments, the step of adjusting the amplitude includes decreasing the amplitude when the patient is responding well to the stimulation of the vagus nerve.

In some embodiments, the method further includes increasing a stimulation interval after the step of adjusting the amplitude of the stimulation to the vagus nerve until at least one of P300, activation of the nucleus basilis, and activation of the locus coeruleus is detected in the EEG.

In some embodiments, a system for stimulating a nerve of a patient is provided. The system can include an implantable nerve stimulator configured to stimulate the nerve of the patient according to a set of programmed stimulation parameters; an EEG recording device configured to record an EEG of the patient; and a controller in communication with both the EEG recording device and the implantable nerve stimulator, the controller programmed to determine whether at least one of P300, activation of the nucleus basalis, and activation of the locus coeruleus is indicated by the EEG, and adjust the set of programmed stimulation parameters based on the determination of whether at least one of P300, activation of the nucleus basalis, and activation of the locus coeruleus is indicated by the EEG.

In some embodiments, the controller is located in a prescription pad.

In some embodiments, the controller is located in an energizer configured to provide power to the implantable nerve stimulator.

In some embodiments, the controller is located in the EEG recording device.

In some embodiments, the set of programmed stimulation parameters includes a pulse amplitude, a pulse width, and a pulse frequency.

In some embodiments, a method for treating a patient suffering from inflammation is provided. The method can include stimulating at least one of the nucleus basalis and the locus coeruleus with an electrode implanted within the patient's brain; and reducing a level of inflammation in the patient.

In some embodiments, the step of stimulating at least one of the nucleus basalis and the locus coeruleus with an electrode implanted within the patient's brain includes delivering an electrical stimulus having a current between 10 to 100 uA, a frequency of 1 to 500 Hz, and a duration of up to 120 minutes.

In some embodiments, a method for treating a patient suffering from inflammation is provided. The method can include stimulating at least one of the nucleus basalis and the locus coeruleus with a focused magnetic field; and reducing a level of inflammation in the patient.

In some embodiments, the step of stimulating at least one of the nucleus basalis and locus coeruleus with the focused magnetic field includes generating the focused magnetic field with a transcranial magnetic coil.

In some embodiments, the step of stimulating at least one of the nucleus basalis and locus coeruleus with the focused magnetic field includes generating the magnetic field with a frequency below 3 Hz, a field strength below 3 Tesla, and a duration between 5 to 60 minutes.

In some embodiments, the step of stimulating at least one of the nucleus basalis and locus coeruleus with the focused magnetic field includes generating the magnetic field with a frequency between 3 to 25 Hz, a field strength below 3 Tesla, and a duration between 5 to 60 minutes.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
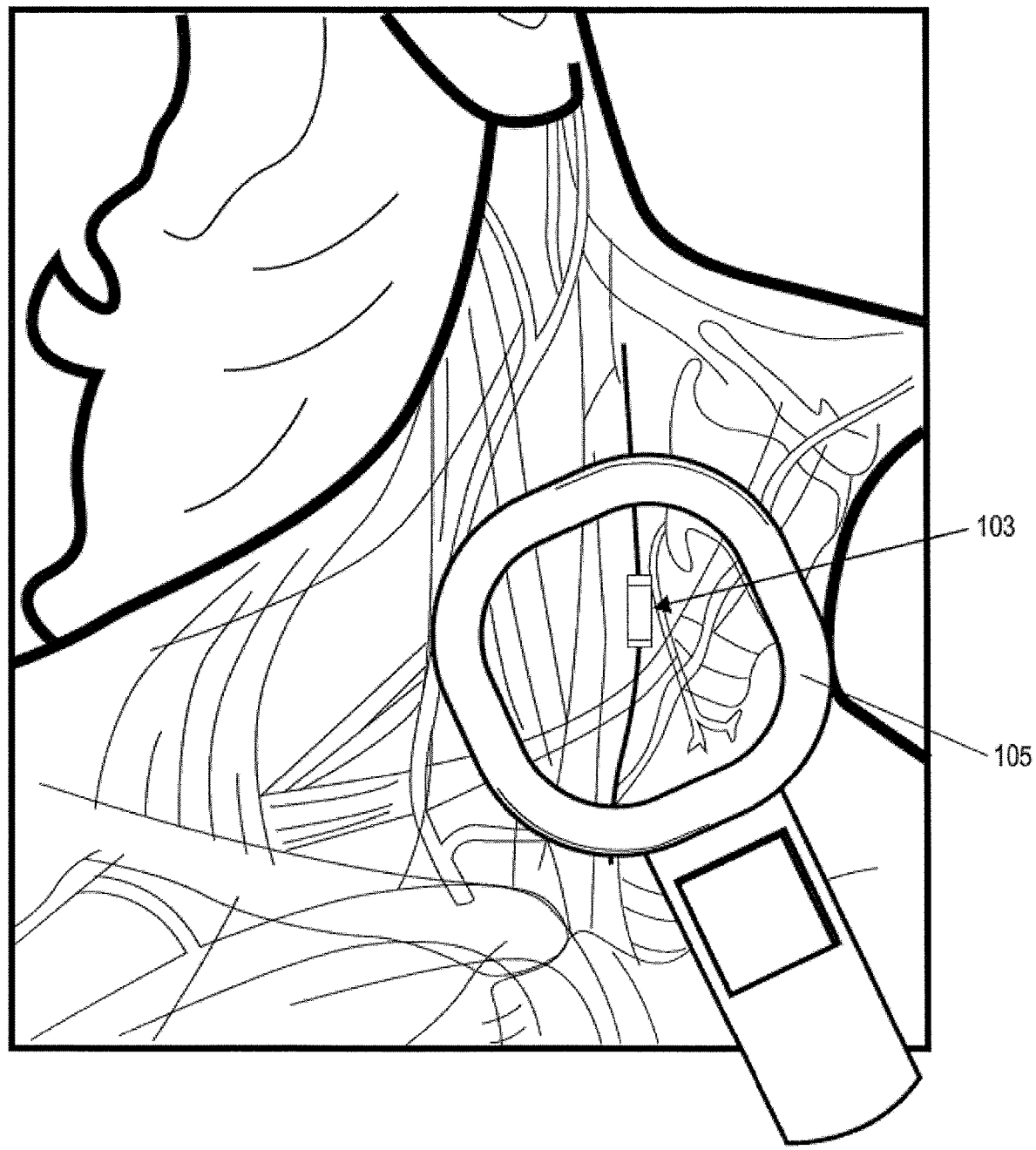
FIG. 1A shows one variation of a system for modulating chronic inflammation including a leadless microstimulator (shown connected to the vagus nerve) and an external charger/controller.

Various regions or neural groups in the brain and central nervous system are linked to the vagus nerve through sympathetic and/or efferent neural pathways. Consequently, activation or stimulation of these regions or neuronal groups may initiate and/or modulate vagus nerve activity. Alternatively, activation or stimulation of the vagus nerve may initiate and/or modulate activity in these various regions or neural groups. Because activation of the vagus nerve may result in activation of the these regions or neural groups, these regions or neural groups can be monitored as surrogates or proxies for determining whether the vagus nerve has been successfully activated by the VNS.

For example, the nucleus basalis (NB) is composed of a neural group in the substantia innominata of the basal forebrain, next to the hypothalamus, and is a source of much of the acetylcholine in the brain. The degradation of the NB has been shown to play a role in Parkinson's and Alzheimer's disease. The NB receives noradrenergic innervation from the locus coeruleus and has neural projections to the caudate nucleus, globus pallidus, thalamus, hippocampus, cerebral cortex, and the brainstem. NB activity drives efferent vagal output [1] and activation of the NB increases attention and cortical plasticity.

Another region, the locus coeruleus (LC), is composed of a neural group located in the pons within the brainstem and is the principle source of norepinephrine (NE) in the brain. The LC has neural inputs from the nucleus tractus solitaries (NTS), dorsal raphe nucleus and projects to the NTS, dorsal raphe nucleus, thalamus, hypothalamus, amygdala, cortex, and the nucleus basalis. Activation of LC increases attention and cortical plasticity. LC coordinates VNS input with sympathetic output.

VNS can be used to activate both NB [2] and LC [3]. VNS causes increased firing within LC that can last for days [4]. VNS enhances recognition memory in humans [5]. Paired VNS (30 Hz, 0.8 mA, 100 uS, 0.5 S, 2.5 hr duration) with tonal training results in reduction of rat tinnitus for more than 24 h [6]. These data show an increase in auditory cortical plasticity in topographically mapped brain regions with synchronous activation of NB and LC by VNS with training.

P300 describes an event-related potential (ERP) component that occur at latencies of about 250-700 msec and can be quantified by EEG recording as a positive voltage deflection. LC activity correlates with P300, as P300 is enhanced when LC activity is enhanced, and LC lesion or inhibition decreases P300 in monkeys [8]. There is a correlation between P300 activation and VNS responders in depression [9].

Therefore, during and/or after VNS, electrical activity from the NB and/or LC, including the P300, can be measured with EEG in order to provide immediate feedback or feedback within seconds or minutes after stimulation, rather than obtaining feedback from reduction in inflammation levels, which may take hours or longer to manifest. In some variations simply detecting the P300 during VNS and/or afterwards is sufficient to provide feedback and/or information. Alternatively, in some variations, the P300 may be detected based on a criterion (e.g., at or above a threshold such as a reference amplitude) before indicating a positive reading (e.g., triggering feedback). If electrical activity and/or the P300 is not detected or does not meet threshold values, the stimulation parameters, such as amplitude, can be adjusted until the electrical activity and/or P300 is detected and meets the threshold values that indicate NB and/or LC activation. It may not be necessary to provide a stimulus other than the VNS to elicit NB or LC activity; for example, any of the methods or apparatuses (systems and devices) described herein may examine the EEG during and/or just after the VNS.

Since P300 is an ERP, a predetermined stimulus can be provided to the patient to elicit P300. In some embodiments, the stimulus is the VNS itself. In other embodiments, the patient can be given a specific sensory, cognitive, or motor stimulus, and the EEG recording between about 250 msec and 700 msec after the stimulus can be analyzed for a positive voltage deflection that represents P300. Examples of a stimulus include an auditory stimulus provided using an auditory oddball paradigm and/or a visual stimulus provided using a visual oddball paradigm. The oddball paradigm presents a series of repetitive audio and/or visual stimuli that are interrupted by a deviant target stimulus, which the patient is asked to detect. Any of these stimuli can also be used to elicit electrical activity from the NB and/or LC.

Vagus Nerve Stimulation System

Systems for electrically stimulating one or more nerves to treat chronic inflammation may include an implantable, wireless microstimulator such as those described herein and an external charging device (which may be referred to as a charging wand, charger, or energizer). In some variations the system also includes a controller such as a "prescription pad" that helps control and regulate the dose delivered by the system. The microstimulator may be secured in position using a securing device (which may be referred to as a "POD") to hold the microstimulator in position around or adjacent to a nerve. These microstimulators are designed and adapted for treatment of chronic inflammation, and may be configured specifically for such use. Thus, an implantable microstimulator may be small, and adapted for the low duty-cycle stimulation to modulate inflammation. For example, the implantable microstimulator may hold a relatively small amount of power over weeks or even months and discharge it at a rate sufficient to modulate the anti-inflammatory pathway without significantly depressing heart rate or triggering any number of unwanted effects from the vagus nerve or other neural connections. Any of the nerves of the inflammatory reflex, including the vagus nerve, may be treated as described herein using the systems described.

For example, FIG. 1A illustrates one variation of a system for treating chronic inflammation that includes a microstimulator contained in POD that is mounted on cervical vagus nerve and charged a programmed by an external charger/programmer unit. This variation of a system includes a microstimulator 103 that has been implanted to contact the vagus nerve as shown. The implant may be programmed, controlled and/or charged by a charger/controller 105 device. In this variation the charger/controller is a loop with a wand region.

Figure 1B:
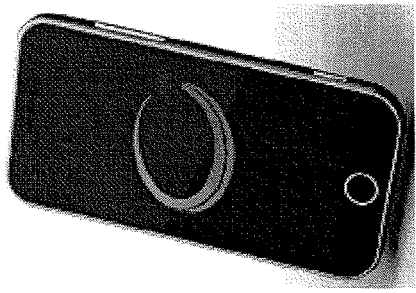
FIG. 1B shows another variation of a system for modulating chronic inflammation, including a microstimulator, charger ("energizer"), and system programmer/controller ("prescription pad").
Figure 1B:
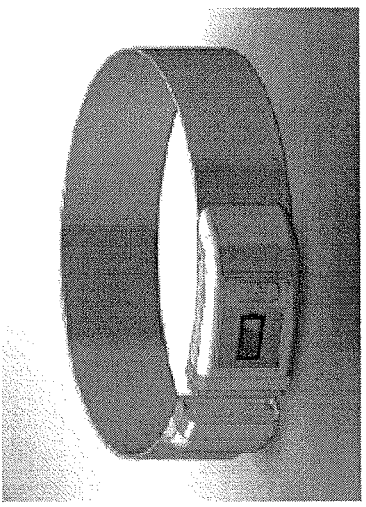
Figure 1B:
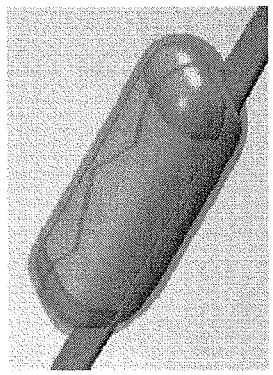

FIG. 1B shows another variation of a system for treating chronic inflammation that also includes an implantable microstimulator 103 (shown inserted into a POD to hold it in position relative to a nerve) and a charging device ("energizer" 105) configured as a collar to be worn around the subject's neck and charge the implant. Optionally, the system may include a prescription pad 107 which may be a separate dedicated device or part of a mobile or other handheld device (e.g., an application to run on a handheld device).

Figure 1C:
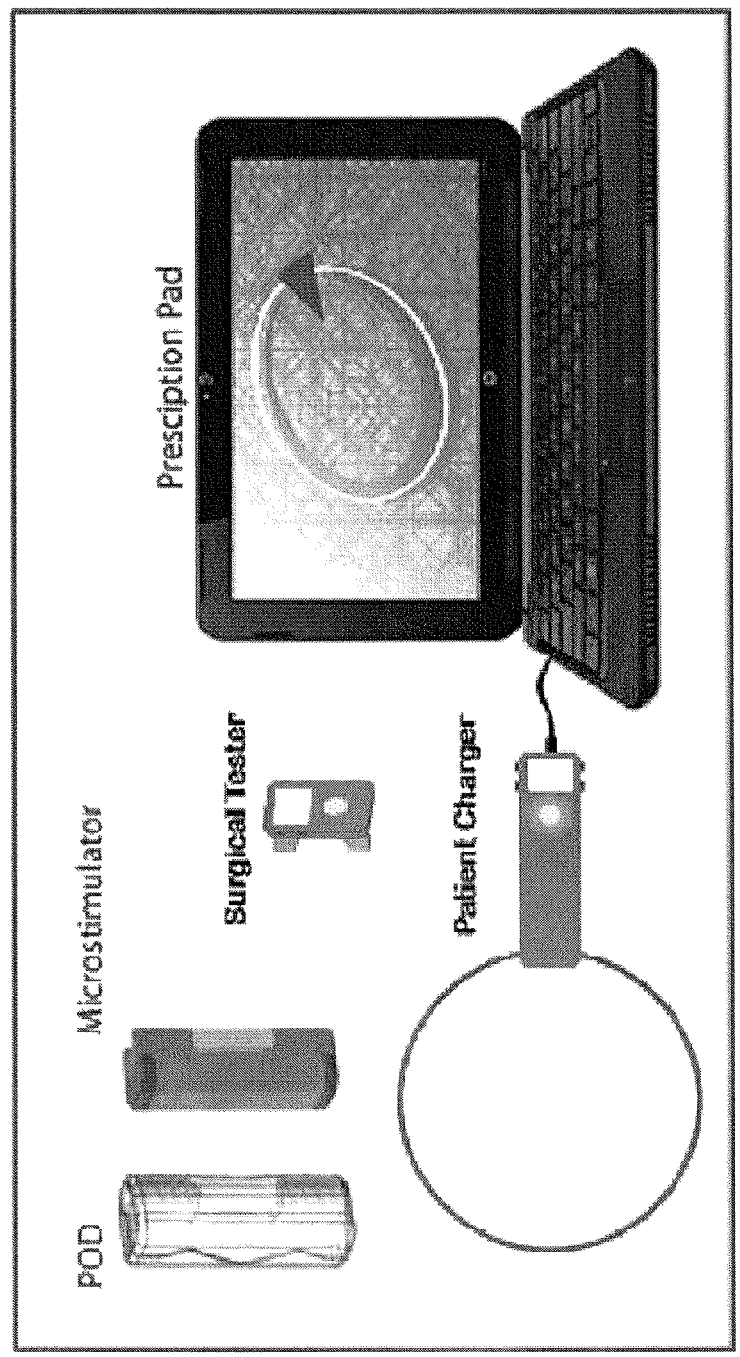
FIG. 1C shows another variations of a system for modulating chronic inflammation, including a microstimulator, a securing device (POD) for securing the leadless stimulator to the nerve, an external charger, a system programmer/controller ("prescription pad") and an optional surgical tester.
Figure 1D:
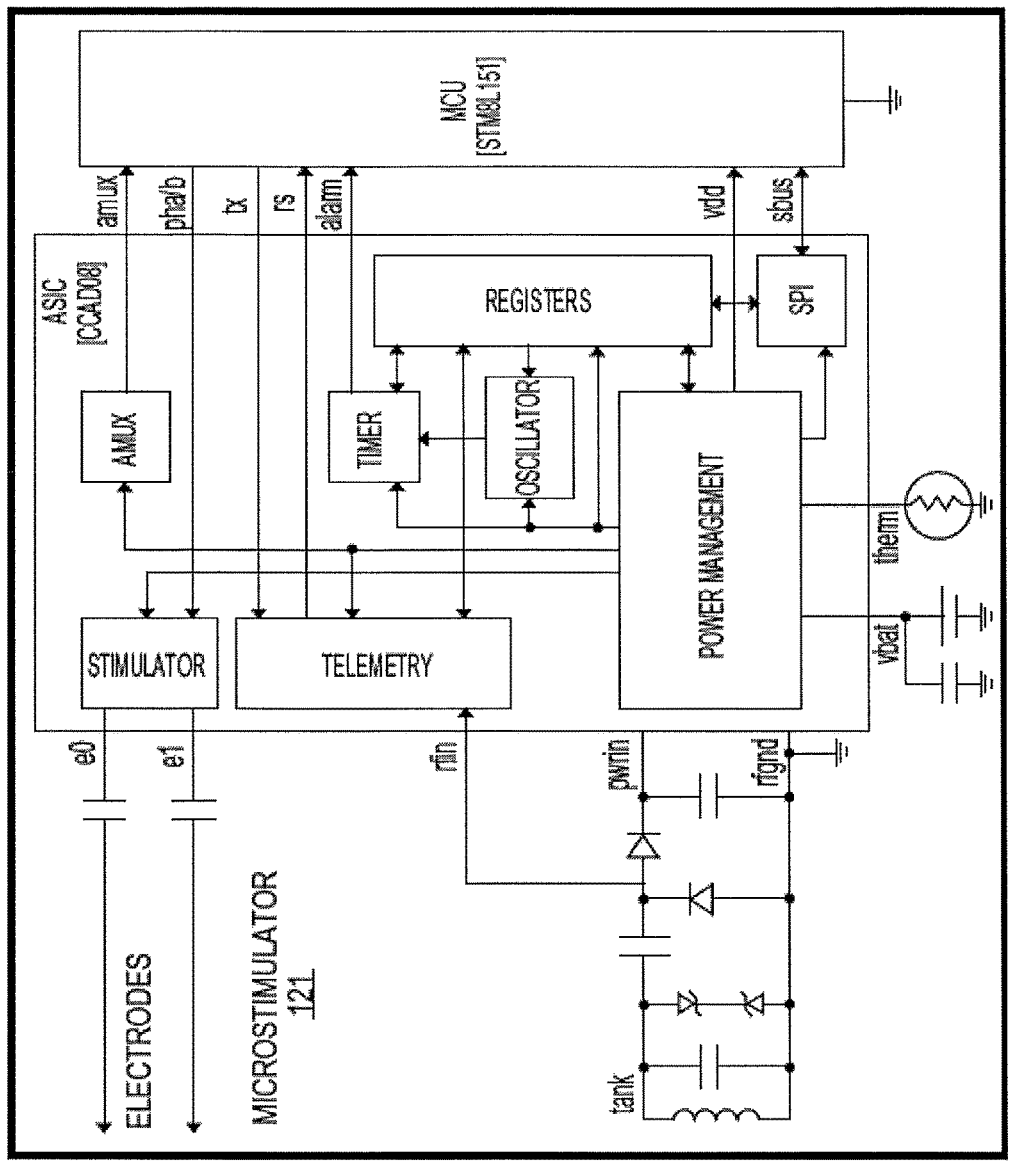
FIG. 1D is a block diagram schematically illustrating the microstimulator and the charger.
Figure 1D:
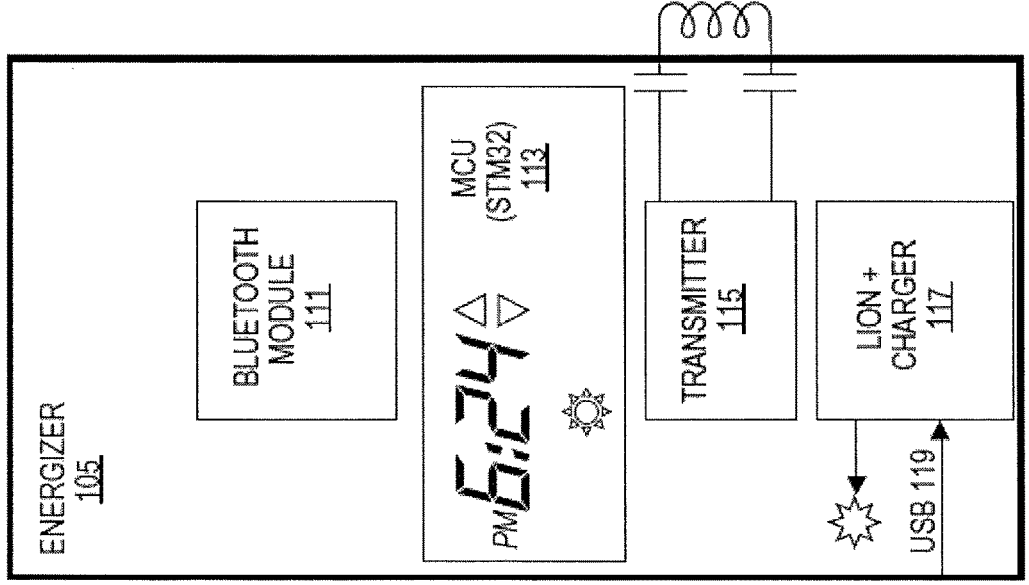

FIG. 1C shows another variation of a system for treating chronic inflammation. The systems described herein may also be referred to as systems for the neural stimulation of the cholinergic anti-inflammatory pathway (NCAP). These systems may be configured as chronic implantable systems.

In some variations, the systems are configured to treat acutely (e.g., acute may 8 hours or less), sub-acutely (expected to occur for fewer than 30 days), or chronically (expected to occur for more than 30 days).

In general, the systems described herein may be configured to apply electrical stimulation at a minimum level necessary to modulate the inflammatory reflex (e.g., modulating cytokine release) characterized by the Chronaxie and rheobase. Chronaxie typically refers to the minimum time over which an electric current double the strength of the rheobase needs to be applied in order to stimulate the neuron. Rheobase is the minimal electrical current of infinite duration that results in an action potential. As used herein, cytokines refer to a category of signaling proteins and glycoproteins that, like hormones and neurotransmitters, are used extensively in cellular communication.

The NCAP Systems described herein are typically intended for the treatment of chronic inflammation through the use of implanted neural stimulation devices (microstimulators) to affect the Neural Stimulation of the Cholinergic Anti-inflammatory Pathway (NCAP) as a potential therapeutic intervention for rheumatologic and other inflammation-mediated diseases and disorders. Neurostimulation of the Cholinergic Anti-inflammatory Pathway (NCAP) has been shown to modulate inflammation. Thus, the treatment and management of symptoms manifested from the onset of disease (e.g., inflammatory disease) is based upon the concept of modulating the Cholinergic Anti-inflammatory Pathway. The NCAP pathway normally maintains precise restraint of the circulating immune cells. As used herein, the CAP is a reflex that utilizes cholinergic nerve signals traveling via the Vagus nerve between the brain, chemoreceptors, and the reticuloendothelial system (e.g., spleen, liver). Local release of pro-inflammatory cytokines (e.g., tumor necrosis factor or TNF) from resident immune cells is inhibited by the efferent, or indirectly by afferent vagus nerve signals. NCAP causes important changes in the function and microenvironment of the spleen, liver and other reticuloendothelial organs. Leukocytes which circulate systemically become "educated" as they traverse the liver and spleen are thereby functionally down regulated by the affected environment of the reticuloendothelial system. This effect can potentially occur even in the absence of an inflammatory condition.

Under this model, remote inflammation is then dampened by down-regulated cytokine levels. Stimulation of the vagus nerve with a specific regiment of electrical pulses regulates production of pro-inflammatory cytokines. In-turn, the down regulation of these cytokines may reduce localized inflammation in joints and other organs of patients with autoimmune and inflammatory disorders.

The NCAP System includes a neurostimulator that may trigger the CAP by stimulating the cervical vagus nerve. The NCAP System issues a timed burst of current controlled pulses with sufficient amplitude to trigger the CAP at a particular interval. These two parameters, Dose Amplitude and Dose Interval, may be used by a clinician to adjust the device. For example, the clinician may set the Dose Amplitude by modifying the current level. The Dose Interval may be set by changing the duration between Doses (e.g. 12, 24, 48 hours).

In some variations, dose amplitude may be set to within the Therapy Window. The Therapy window is defined as the lower limit of current necessary to trigger the CAP, and the upper limit is the level at which the Patient feels uncomfortable. The lower limit is called the Threshold (T), and the uncomfortable level is called Upper Comfort Level (UCL).

Dose Amplitude thresholds are nonlinearly dependent upon Current (I), Pulse width (PW), Pulse Frequency (PF), and Burst Duration (BD). Amplitude is primarily set by charge (Q), that is Current (I)×Pulse width (PW). In neurostimulation applications current has the most linear relationship when determining thresholds and working within the therapy window. Therefore, the clinician may modify Dose Amplitude by modifying current. The other parameters are held to experimentally determined defaults. Pulse width is selected to be narrow enough to minimize muscle recruitment and wide enough to be well above the chronaxie of the targeted neurons. Stimulus duration and pulse frequency was determined experimentally in Preclinical work.

Dose Interval may be specific for particular diseases and the intensity of diseases experienced by a patient. Our initial research has indicated that the cervical portion of the vagus nerve may be an ideal anatomic location for delivery of stimulation. The nerve runs through the carotid sheath parallel to the internal jugular vein and carotid artery. At this location, excitation thresholds for the vagus are low, and the nerve is surgically accessible. We have not found any significant difference in biomarker modulation (e.g., modulation of cytokines) between right and left. Even though the right vagus is thought to have lower thresholds than the left in triggering cardiac dysrythmias, the thresholds necessary for NCAP are much lower than those expected to cause such dysrythmias. Therefore a device delivering NCAP can safely be applied to either the right or left vagus.

We have also found, surprisingly, that the Therapy Window is maximized on the cervical vagus through the use of a bipolar cuff electrode design. Key parameters of the cuff may be: spacing and shielding of the contacts. For example, the contact points or bands may be spaced 1-2 diameters of the vagus nerve apart, and it may be helpful to shield current from these contacts from other nearby structures susceptible to inadvertent triggering. The cuff may be further optimized by using bands which are as long and wide as possible to reduce neurostimulator power requirements.

Figure 3A:
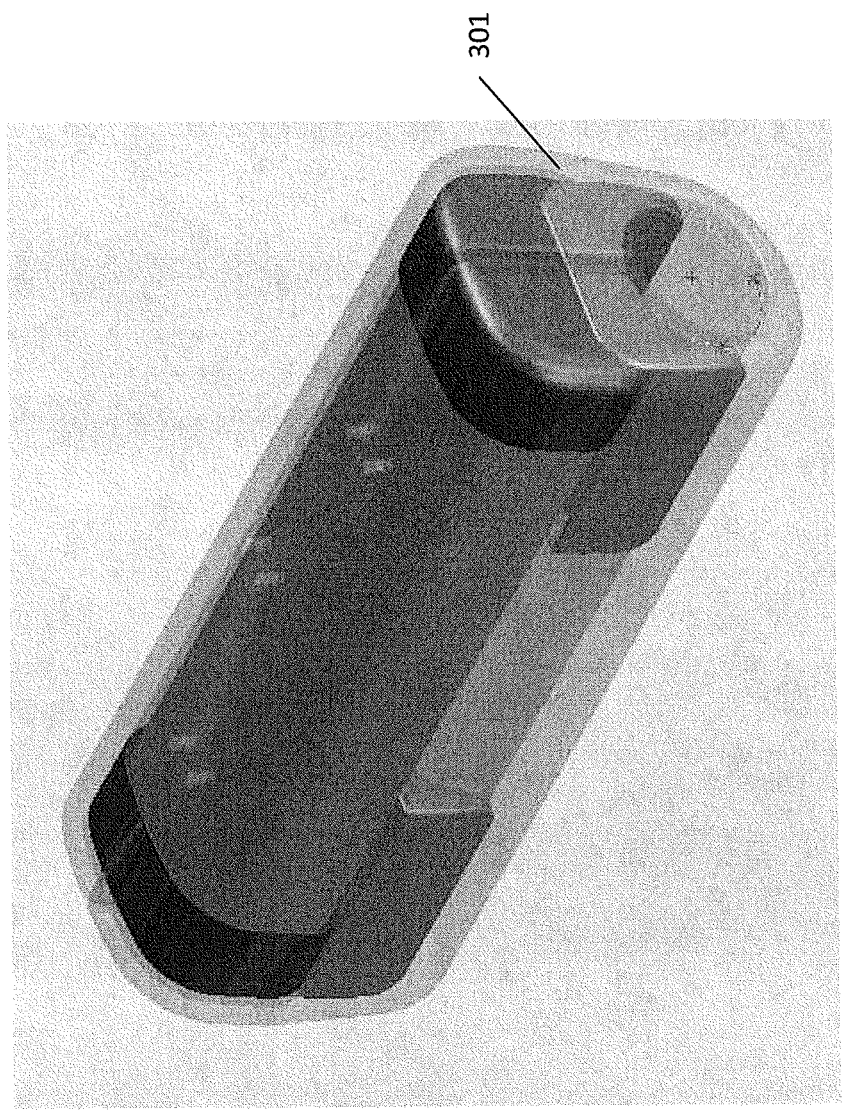
FIG. 3A shows one variation of a microstimulator in a POD configured to surround a nerve of the inflammatory reflex.
Figure 3B:
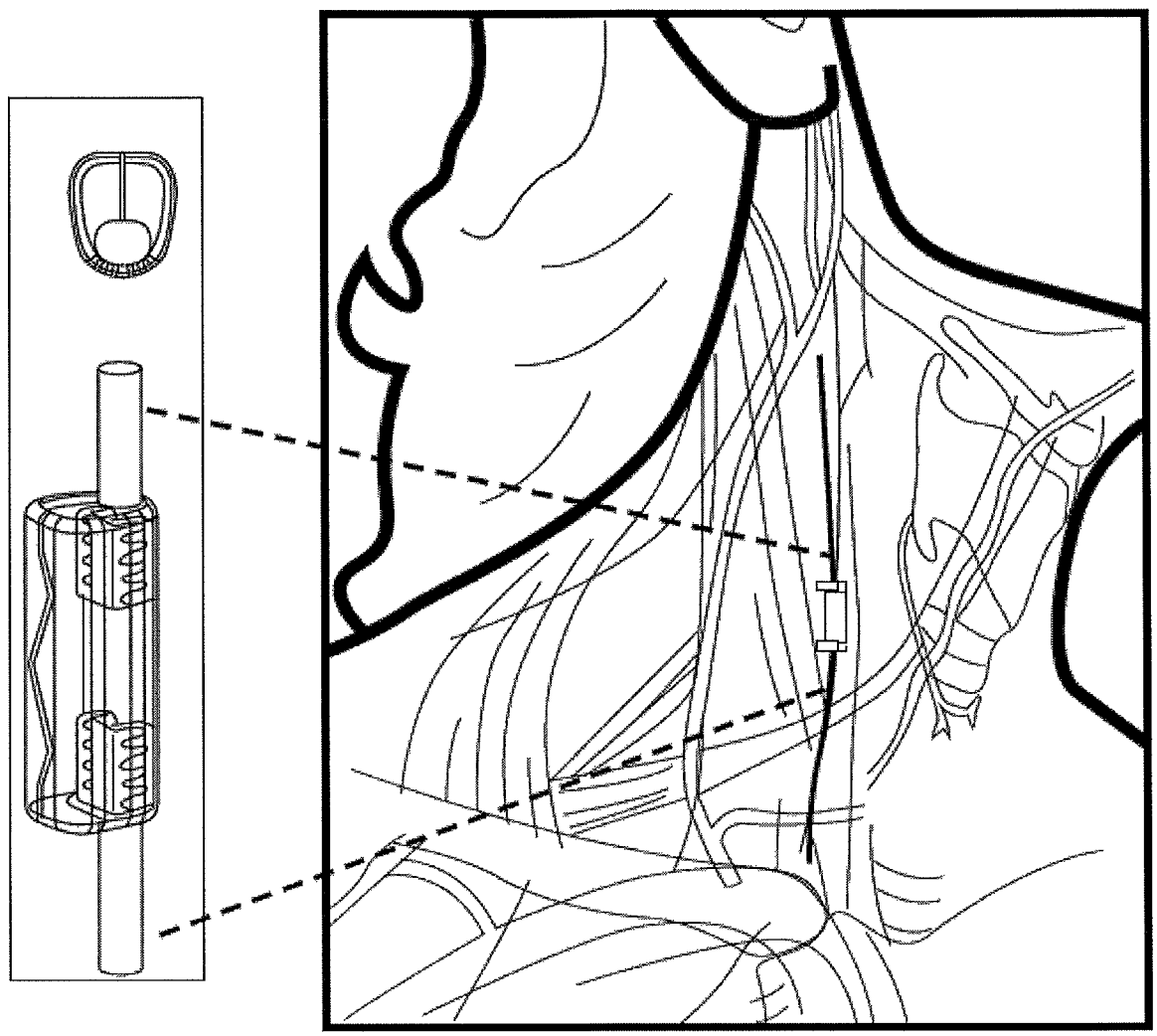
FIG. 3B shows an enlarged view of the microstimulator and POD.
Figure 3D:
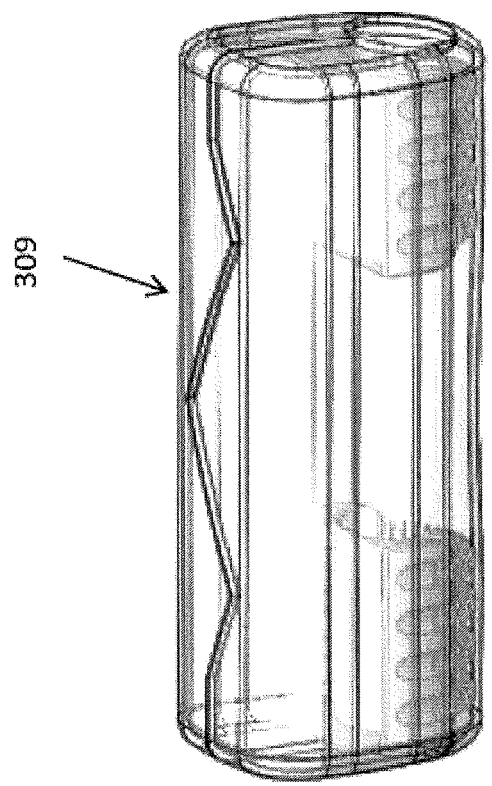
FIG. 3D shows the microstimulator of FIG. 3C within a POD.
Figure 3C:
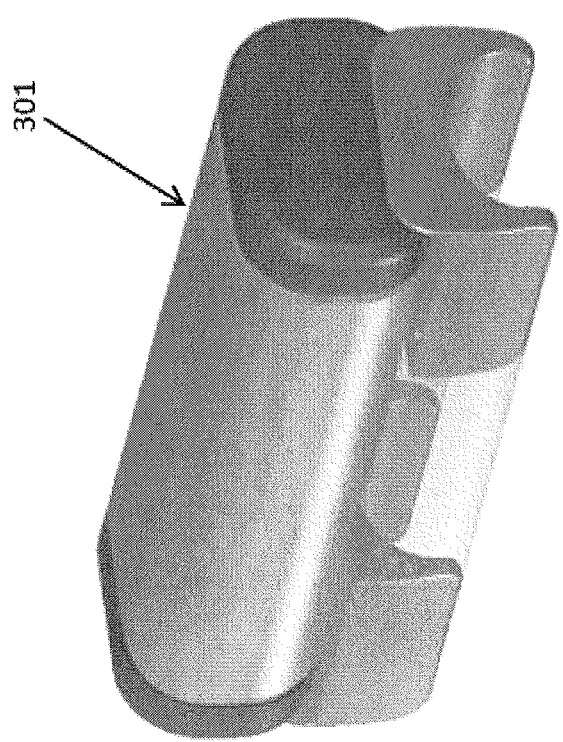
FIG. 3C shows another variation of a microstimulator.

Thus, any variations of the systems described herein (e.g., the NCAP system) may be implemented with a Cuff, Lead and Implantable Pulse Generation (IPG), or a Leadless Cuff. The preferred implementation is a leadless cuff implemented by a microstimulator with integral electrode contacts in intimate contact with the nerve and contained within a Protection and Orientation Device (POD). This is illustrated in FIGS. 3A and 3B. The POD 301 may form a current shield, hold the microstimulator into place against the vagus nerve, and extend the microstimulator integral contacts with integral contacts in the POD itself. The POD is typically a polymer shell that encapsulates a microstimulator implant and that allows a nerve to run through the interior against the shell wall parallel to the length of the microstimulator implant. Within the shell of the POD, the microstimulator implant remains fixed against the Vagus nerve so the electrodes remain in contact with the nerve. The POD anchors the implant in place and prevents the implant from rotating or separating from the nerve, as well as maintaining contact between the electrodes and the nerve and preserving the orientation as necessary for efficient external charging of the microstimulator battery.

Referring back to FIG. 1C, the system may include an implantable microstimulator contained in a POD, a Patient Charger, and a prescription pad that may be used by the clinician to set dosage parameters for the patient. This system may evaluate the efficacy, safety, and usability of an NCAP technology for chronic treatment of clinical patients.

The system can employ a Prescription Pad (external controller) that may include the range of treatment options.

As described in more detail in U.S. Ser. No. 12/874,171 (titled "PRESCRIPTION PAD FOR TREATMENT OF INFLAMMATORY DISORDERS"), previously incorporated by reference in its entirety, the Prescription Pad may incorporate workflows in a simplified interface and provide data collection facilities that can be transferred to an external database utilizing commercially robust and compliant methods and procedures. In use, the system may be recommended for use by a clinician after assessing a patient; the clinician may determine that treatment of chronic inflammation is warranted. The clinician may then refer the patient to an interventional doctor to implant the microstimulator. Thereafter then clinician (or another clinician) may monitor the patient and adjust the device via a wireless programmer (e.g. prescription pad). The clinician may be trained in the diagnosis and treatment procedures for autoimmune and inflammatory disorders; the interventional placement of the system may be performed by a surgeon trained in the implantation of active neurostimulation devices, with a sufficient depth of knowledge and experience regarding cervical and vagal anatomy, experienced in performing surgical dissections in and around the carotid sheath.

The system may output signals, including diagnostics, historical treatment schedules, or the like. The clinician may adjust the device during flares and/or during routine visits. Examples of implantation of the microstimulator were provided in U.S. patent application Ser. No. 12/874,171, which is herein incorporated by reference in its entirety. For example, the implant may be inserted by making an incision in the skin (e.g., ≈3 cm) along Lange's crease between the Facial Vein and the Omohyoid muscle, reflecting the Sternocleidomastoid and gaining access to the carotid sheath. The IJV may be displaced, and the vagus may be dissected from the carotid wall (≤2 cm). A sizing tool may be used to measure the vagus, and an appropriate Microstimulator and POD Kit (small, medium, large) may be selected. The POD may then be inserted under nerve with the POD opening facing the surgeon, so that the microstimulator can be inserted inside POD so that the microstimulator contacts capture the vagus. The POD may then be sutured shut. In some variations a Surgical Tester may be used to activate the microstimulator and perform system integrity and impedance checks, and shut the microstimulator off, during or after the implantation. In other variations the surgical tester may be unnecessary, as described in greater detail below.

A physician may use the Patient Charger to activate the microstimulator, perform integrity checks, and assure sufficient battery reserve exists. Electrodes may be conditioned with sub-threshold current and impedances may be measured. A Physician may charge the microstimulator. In some variations a separate charger (e.g., an "energizer") may be used by the patient directly, separate from the controller the physician may use. Alternatively, the patient controller may include controls for operation by a physician; the system may lock out non-physicians (e.g., those not having a key, code, or other security pass) from operating or modifying the controls.

In general, a physician may establish safe dosage levels. The physician may slowly increment current level to establish a maximum limit (Upper Comfort Limit). This current level may be used to set the Dosage Level. The exact procedure may be determined during this clinical phase.

The Physician may also specify dosing parameters that specify dosage levels and dosage intervals. The device may contain several concurrent dosing programs which may be used to acclimate the patient to stimulus, gradually increase dosage until efficacy is achieved, reset tachyphylaxis, or deal with unique patient situations.

Figure 2:
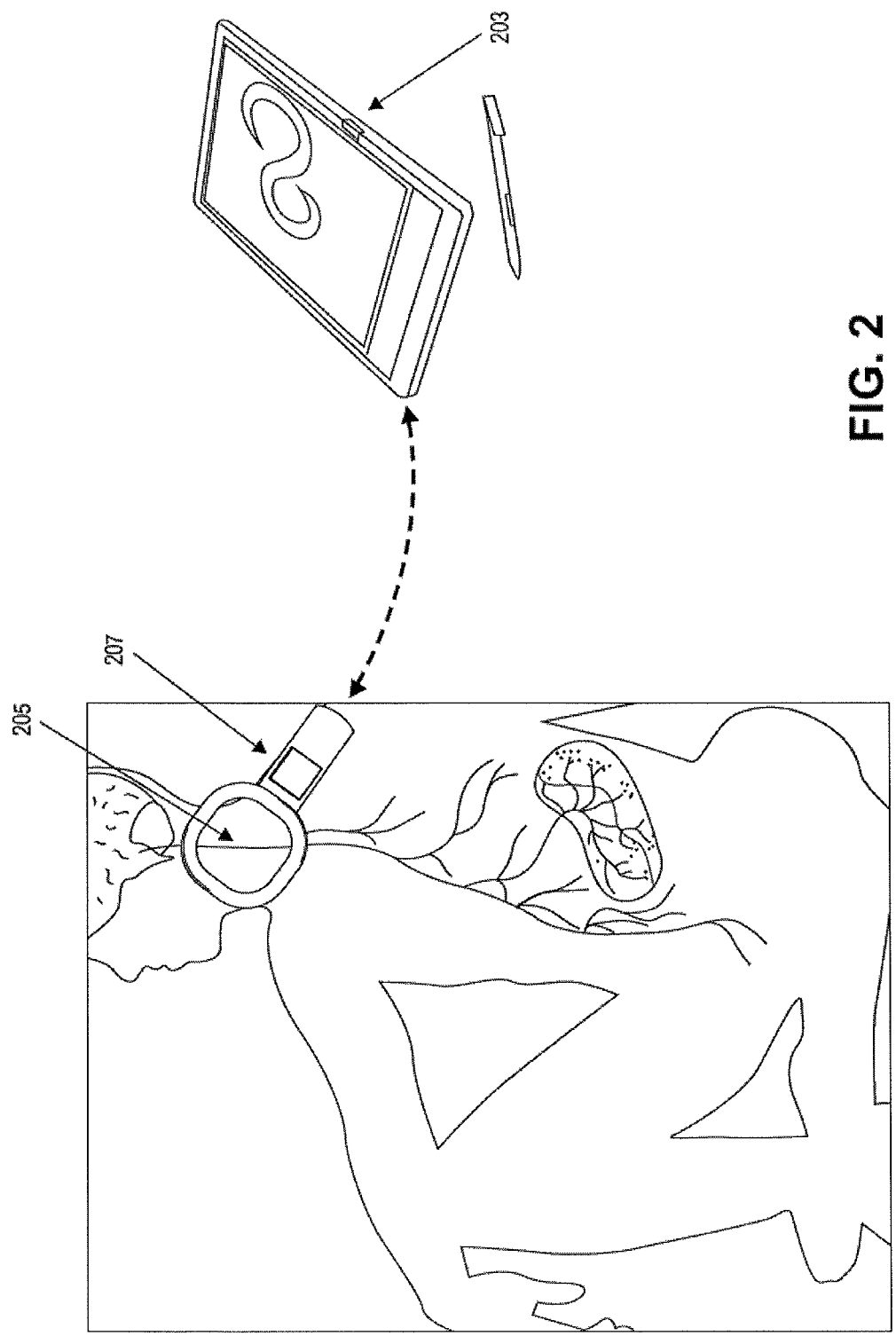
FIG. 2 illustrates one variation of an external system programmer/controller wirelessly connected to a microstimulator.

In some variations, the Prescription Pad may be configured to handle multiple patients and may index their data by the microstimulator Serial Number. For example, a Prescription Pad may handle up to 100,000 patients and 10,000 records per patient, and may store the data in its local memory and may be backed up on an external database. In some variations, during each charging session, accumulated even log contents will be uploaded to the Patient Charger for later transfer to Prescription Pad. The data may or may not be cleared from the microstimulator. For example, FIG. 2 shows the addition of a prescription pad 203 wirelessly connected to the charger/programmer 207.

The microstimulators described herein are configured for implantation and stimulation of the cholinergic anti-inflammatory pathway, and especially the vagus nerve. In particular the microstimulators described herein are configured for implantation in the cervical region of the vagus nerve to provide extremely low duty-cycle stimulation sufficient to modulate inflammation. These microstimulators may be adapted for this purpose by including one or more of the following characteristics, which are described in greater detail herein: the conductive capsule ends of the microstimulator may be routed to separate electrodes; the conductive capsule ends may be made from resistive titanium alloy to reduce magnetic field absorption; the electrodes may be positioned in a polymer saddle; the device includes a suspension (e.g., components may be suspended by metal clips) to safeguard the electronics from mechanical forces and shock; the device may include an H-bridge current source with capacitor isolation on both leads; the device may include a built in temperature sensor that stops energy absorption from any RF source by detuning the resonator; the device may include a built-in overvoltage sensor to stop energy absorption from any RF source by detuning resonator; the system may include DACs that are used to calibrate silicon for battery charging and protection; the system may include DACs that are used to calibrate silicon for precision timing rather than relying on crystal oscillator; the system may include a load stabilizer that maintains constant load so that inductive system can communicate efficiently; the system may include current limiters to prevent a current rush so that the microstimulator will power up smoothly from resonator power source; the system may extract a clock from carrier OR from internal clock; the device may use an ultra-low power accurate RC oscillator that uses stable temperature in body, DAC calibration, and clock adjustment during charging process; the device may use a solid state UPON battery that allows fast recharge, supports many cycles, cannot explode, and is easy to charge with constant voltage; and the device may include a resonator that uses low frequency material designed not to absorb energy by high frequency sources such as MRI and Diathermy devices.

Many of these improvements permit the device to have an extremely small footprint and power consumption, while still effectively modulating the vagus nerve.

FIG. 3A is a perspective drawing of the Pod containing the microstimulator. Sutures (not shown) are intended to be bridged across one to three sets of holes. Electrodes integrated into the pod are not shown but would extend as bands originating and ending on the two outer pairs of suture holes.

Figure 3E:
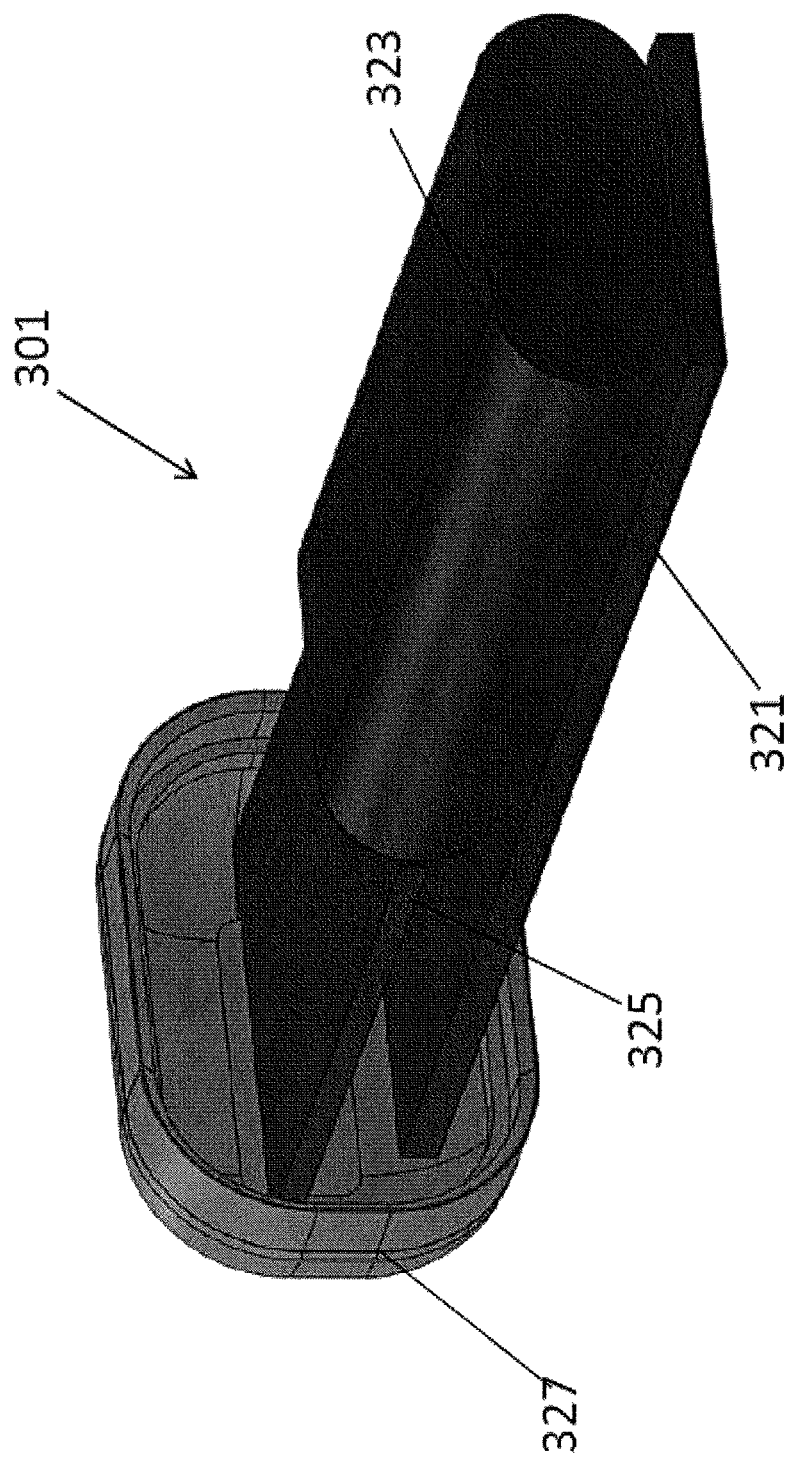
FIG. 3E shows another variation of the microstimulator.

In some variations, including those described above, the microstimulator consists of a ceramic body with hermetically sealed titanium-niobium ends and integral platinum-iridium electrodes attached. The microstimulator may be designed to fit within a POD 309, as shown in FIGS. 3A-3D. As described above, the POD is a biocompatible polymer with integrated electrodes that may help the microstimulator to function as a leadless cuff electrode. In some variations, such as the variation shown in FIG. 3E, contained within the hermetic space of the microstimulator 301 is an electronic assembly that contains a rechargeable battery 321, solenoid antenna 323, hybrid circuit 325 and electrode contacts (Ti Alloy braze ring and end cap) 327 at each end to make contact with the titanium/platinum case ends.

In some embodiments, the microstimulator can be batteryless. The batteryless microstimulator can be powered inductively by an external power source to deliver an electrical stimulus to the nerve. In some embodiments, the batteryless microstimulator can have a capacitor or supercapacitor instead of a battery for storing energy which can be released as an electrical stimulus.

Figure 4:
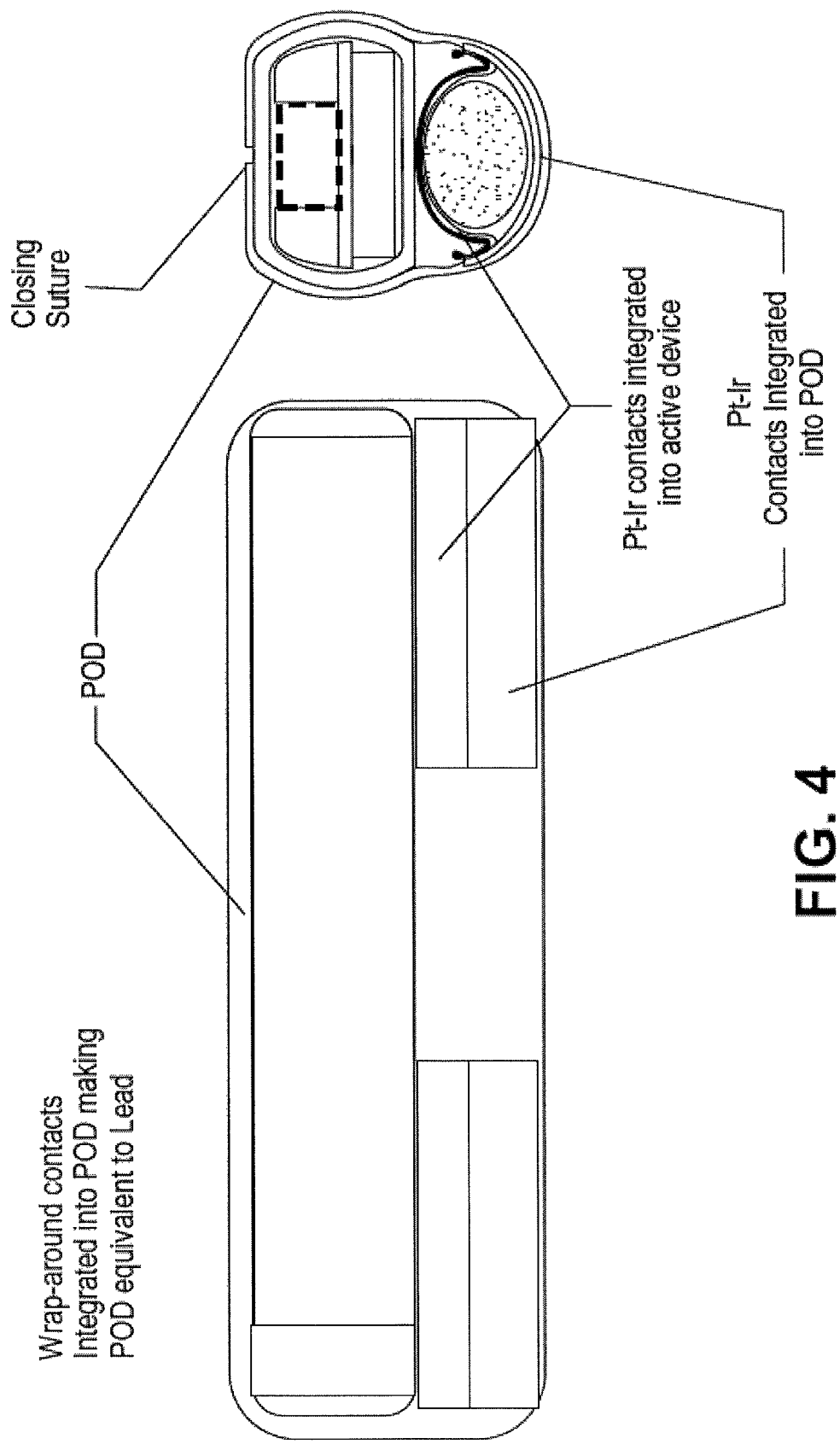
FIG. 4 shows a schematic diagram of a microstimulator and POD around vagus nerve.

As mentioned above, some of the device variations described herein may be used with a POD to secure the implant (e.g., the leadless/wireless microstimulator implant) in position within the cervical region of the vagus nerve so that the device may be programmed and recharged by the charger/programmer (e.g., "energizer"). For example, FIG. 4 shows a schematic diagram of a POD containing a microstimulator. The cross section in FIG. 4 shows the ceramic tube containing electronic assembly that includes the hybrid, battery and coil. The rigid or semi-rigid contacts are mounted on the tube and surround the oval vagus nerve. The POD surrounds the entire device and includes a metal conductor that makes electrical contact with the microstimulator contacts and electrically surrounds the nerve.

In some variations, the microstimulator may have a bipolar stimulation current source that produce as stimulation dose with the characteristics shown in table 1, below. In some variation, the system may be configured to allow adjustment of the "Advanced Parameters" listed below; in some variations the parameters may be configured so that they are predetermined or pre-set. In some variations, the Advanced Parameters are not adjustable (or shown) to the clinician. All parameters listed in Table 1 are ±5% unless specified otherwise.

TABLE 1

| Microstimulator parameters | | |
|---|---|---|
| Property | Value | Default |
| Dosage Amplitude (DA) | 0-5,000 µA in 25 µA steps | 0 |
| Intervals | Minute, Hour, Day, Week, Month | Day |
| Number of Doses per Interval | N = 60 Maximum | 1 |
| Advanced Parameters | | |
| Pulse width Range (PW) | 100-1,000 µS in 50 µS increments | 200 |
| Stimulus Duration (SD) | 0.5-1000 seconds per dose | 60 |
| Pulse Frequency (PF) | 1-50 Hz | 10 |
| Stimulus Voltage (SV) | ±3.3 or ±5.5 ±1 Volts | Automatically set by software |
| Constant Current Output | ±15% over supported range of load impedances (200-2000 Ω) | |
| Specific Dose | Set a specific time between | Driven by default |

TABLE 1-continued

Microstimulator parameters

| Property | Value | Default |
|---|---|---|
| Time | 12:00 am-12:00 am in one minute increments for each Dose Issue | table (TBD) |
| Number of Sequential Dosing Programs | 4 maximum | 1 |

The Dosage Interval is defined as the time between Stimulation Doses. In some variations, to support more advanced dosing scenarios, up to four 'programs' can run sequentially. Each program has a start date and time and will run until the next program starts. Dosing may be suspended while the Prescription Pad is in Programming Mode. Dosing may typically continue as normal while charging. Programs may be loaded into one of four available slots and can be tested before they start running. Low, Typical, and High Dose schedules may be provided. A continuous application schedule may be available by charging every day, or at some other predetermined charging interval. For example, Table 2 illustrates exemplary properties for low, typical and high dose charging intervals:

TABLE 2 low typical and high dose charging intervals

| Property | Value |
|---|---|
| Low Dose Days Charge Interval | 30 days max: 250 μA, 200 μS, 60 s, 24 hr, 10 Hz, ±3.3 V |
| Typical Dose Charge Interval | 30 days max: 1,000 μA, 200 μS, 120 s, 24 hr, 10 Hz, ±3.3 V |
| High Dose Charge Interval | 3.5 days max: 5,000 μA, 500 μS, 240 s, 24 hr, 20 Hz, ±5.5 V, |

The system may also be configured to limit the leakage and maximum and minimum charge densities, to protect the patient, as shown in Table 3:

TABLE 3 safety parameters

| Property | Value |
|---|---|
| Hardware DC Leakage Protection | <50 nA |
| Maximum Charge Density | 30 μC/cm$^2$/phase |
| Maximum Current Density | 30 mA/cm$^2$ |

In some variations, the system may also be configured to allow the following functions (listed in Table 4, below):

TABLE 4

Additional functions of the microstimulator and/or controller(s)

| Function | Details |
|---|---|
| Charging | Replenish Battery |
| Battery Check | Determine charge level |
| System Check | Self Diagnostics |
| Relative Temperature | Temperature difference from baseline |

TABLE 4-continued

Additional functions of the microstimulator and/or controller(s)

| Function | Details |
|---|---|
| Program Management | Read/Write/Modify a dosage parameter programs |
| Program Up/Download | Transfer entire dosage parameter programs |
| Electrode Impedances | Bipolar Impedance (Complex) |
| Signal Strength | Strength of the charging signal to assist the patient in aligning the external Charge to the implanted Microstimulator. |
| Patient Parameters | Patient Information |
| Patient History | Limited programming and exception data |
| Implant Time/Zone | GMT + Time zone, 1 minute resolution, updated by Charger each charge session |
| Firmware Reload | Boot loader allows complete firmware reload |
| Emergency Stop | Disable dosing programs and complete power down system until Prescription Pad connected |

Figure 11:
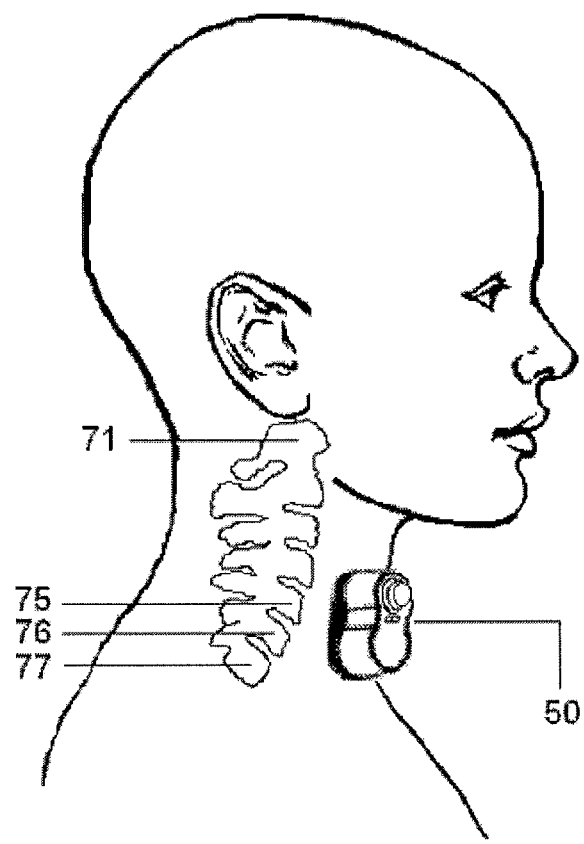
FIG. 11 illustrates an embodiment of a transcutaneous electrical nerve stimulator.

In some embodiments as shown in FIG. 11, a transcutaneous electrical nerve stimulator 50 can be used to stimulate the vagus nerve. An example of a transcutaneous electrocial nerve stimulator is described in U.S. Pat. No. 8,843,210 to Simon et al., which is herein incorporated by reference in its entirety for all purposes. The transcutaneous electrical nerve stimulator can be used in place of the implanted microstimulator, or it can be used along with the implanted microstimulator. FIG. 11 illustrates one placement of the stimulator 50 to a target location on the patient's neck. For reference, locations of the following vertebrae are also shown: first cervical vertebra 71, the fifth cervical vertebra 75, the sixth cervical vertebra 76, and the seventh cervical vertebra 77.

EEG Recording System

Figure 5:
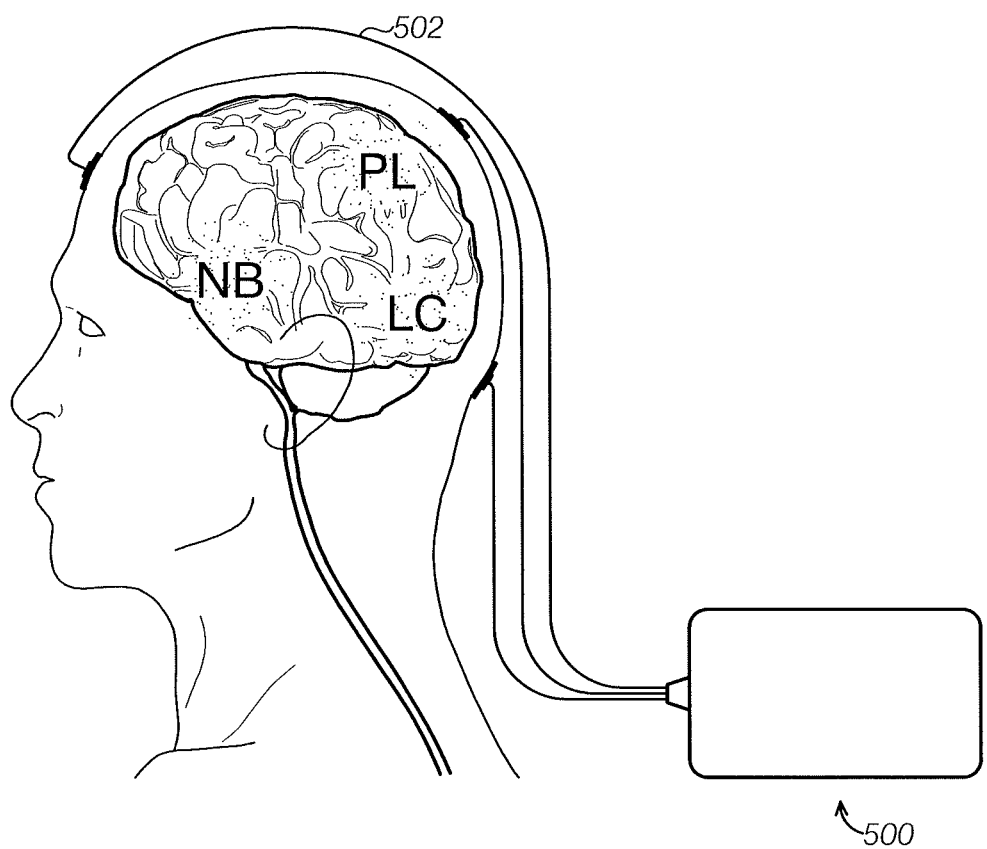
FIG. 5 illustrates an embodiment of an EEG recording system for detecting P300 and/or activation of the locus coeruleus and/or nucleus basalis.

FIG. 5 illustrates an EEG recording device 500 with electrodes 502 placed proximate the brain regions of interest, such the NB and/or LC, can be used to record the patient's EEGs. For example, one or more electrodes can be placed on the patient's forehead over the basal forebrain to record EEGs from the NB, while one or more electrodes can be placed on the lower back portion of the patient's head over the brainstem to record EEGs from the LC. P300 can be measured from electrodes being used to measure the NB and/or LC, and/or can be measured from electrodes placed over the parietal lobe. A baseline EEG can be recorded before VNS to serve as a comparison for EEGs measured after VNS.

In some embodiments, the EEG recording device may be programmed to detect and analyze P300 and/or activation of the NB and/or LC. In some embodiments, the analysis of the data from the EEG recording device can be accomplished with a separate computing device programmed to do the task. In some embodiments, the results of this analysis can be communicated to a controller that can adjust one or more stimulation parameters based on the analysis of P300 and/or activation of the NB and/or LC. The controller can be located on the microstimulator, the prescription pad, the energizer, the EEG recording device, or a separate computing device.

Prescreening Patients Using EEG

Activation of the Nucleus Basalis and/or the Locus coeruleus and/or detection of P300, all of which can be detected and/or measured with an EEG, can be used to prescreen subjects likely respond to VNS treatment prior to implantation. EEG recordings can be measured during or following stimulation of the auricular branch of the vagus nerve, or independent of any additional stimulus. The stimulation of the auricular branch of the vagus nerve can be accomplished through electrical stimulation or mechanical stimulation. In some embodiments, the stimulation can be noninvasive. For example, the electrical stimulation or mechanical stimulation can be delivered through the skin by a stimulation device placed on the skin surface of the ear. Alternatively, the stimulation can be invasive using, for example, a needle electrode to deliver electrical stimulation directly to the nerve.

During or after stimulation of the auricular branch of the vagus nerve, EEG recordings can be taken of the NB and/or LC and the presence of P300 can be detected in the EEG recordings. In some embodiments, at least some of the EEG recordings can be taken after VNS without providing any other additional stimulation to elicit P300 or activity in the NB and/or LC. In some embodiments, at least some of the EEG recordings can be taken while eliciting P300 using a predetermined protocol, such as the auditory and/or visual stimulation oddball protocol. If the EEG recordings show activation of the NB and/or the LC and/or P300 is detected in the EEG recordings, then it is likely that the vagus nerve responded to the stimulation and the patient is a suitable candidate for VNS therapy. In some embodiments, for the analysis, a comparison can be made with reference to EEG recordings taken before VNS therapy.

Use case example: A subject with rheumatoid arthritis is being screened for likelihood of response VNS treatment. The physician will record P300 and EEG measurements of activation of the Nucleus Basalis and/or the Locus coeruleus during electrical stimulation of the subject's auricular branch of the vagus nerve at maximum tolerated current intensity. The subject will pass the screen should P300 and/or activation of the Nucleus Basalis and/or the Locus coeruleus be detected.

Long Term Potentiation

It has been postulated that analogous to somatotopically organized brain regions that sense pain, there exists an immunological homunculus, whereby the immune system acts as a sensory organ that maps to specific regions within the central nervous system at the terminal of the afferent arm of the inflammatory reflex [7]. As activity within the NB and LC can be induced by VNS, and VNS induces long lasting plasticity within the auditory cortex via activation of the NB and LC, we reasoned that plasticity within the central neural reflexes, in part by this immunological homunculus may be induced by VNS activation of the NB and LC as well.

Therefore, VNS activation of the NB and/or the LC can induce long term potentiation of the inflammatory reflex. Typical VNS parameters include an amplitude of 0.1-3 mA, frequency of 1 Hz-30 Hz, pulse width of 100 uS-500 uS, duration of 0.5 second to 10 minutes in duration. The off time between stimulations can be greater than 2, 4, 8, 12, 24, and 48 hours. These parameters are suitable for use in any of the embodiments described herein. For example, a 100 us charge balanced biphasic pulse can be delivered with a current of 0.8 mA as a train of 15 pulses at 30 Hz with a 500 ms train duration. The amplitude and other parameters can be ramped up over time, maintained at a constant level, or be modulated based on feedback, which can be based on NB and/or LC activity and/or detection of P300, for example. NB and/or LC and/or P300 activity can be detected by monitoring, measuring, and/or quantifying electrical activity from those brain regions with EEG recordings.

Feedback Control of VNS

EEG measurements of P300, and/or EEG measurements to detect activation of the Nucleus Basalis and/or the Locus coeruleus can be used to provide immediate or rapid feedback on stimulation parameters during programming or reprogramming of an implanted VNS device. Various stimulation parameters may be increased, decreased or otherwise adjusted until activation of NB, LC or P300 is detected. Feedback control can be used in an open loops system or a closed loop system as described below.

Figure 6:
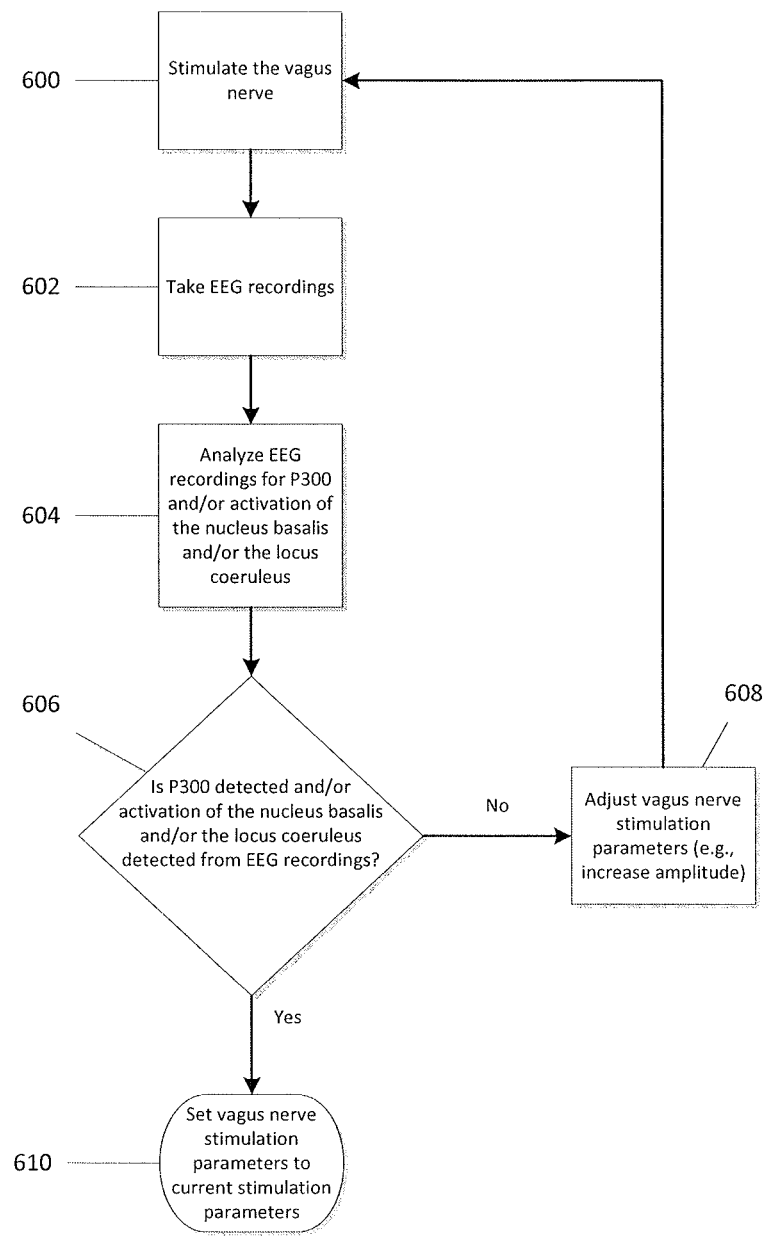
FIG. 6 illustrates a flow chart that describes a method for modulating vagus nerve stimulation using feedback from EEG recordings.

FIG. 6 illustrates a flow chart that describes a method for modulating vagus nerve stimulation using feedback from EEG recordings. For example, this flow chart can be used to treat a patient that is not responding well to VNS treatment. The vagus nerve can be stimulated in step 600 and then EEG recordings can be taken in step 602. The EEG recordings can be taken during the VNS, and can also be taken after the VNS. Next, in step 604, the EEG is analyzed for P300 and/or activation of the NB and/or LC. In some embodiments, the analysis can be performed by a physician, while in other embodiments, the analysis can be performed by a computing device with filters and algorithms tailored to detecting those specific EEG features. At step 606, a decision is made based on the analysis in step 604 whether P300 is detected and/or activation of the NB and/or the LC is detected from the EEG recordings. If P300 and/or activation of the NB and/or the LC is not detected, then the VNS parameters are adjusted, by for example increasing the amplitude and/or the duration of the stimulation in step 608. After the VNS parameters are adjusted, the process loops back to step 600. If at step 606 it is determined that P300 is detected and/or activation of the NB and/or LC is detected, then the VNS parameters can be set to the current stimulation parameters. In some embodiments, this can be performed manually by the physician or health care provider, while in other embodiments, the parameters can be set automatically by a computing device performing the analysis of the EEG recordings.

Figure 7:
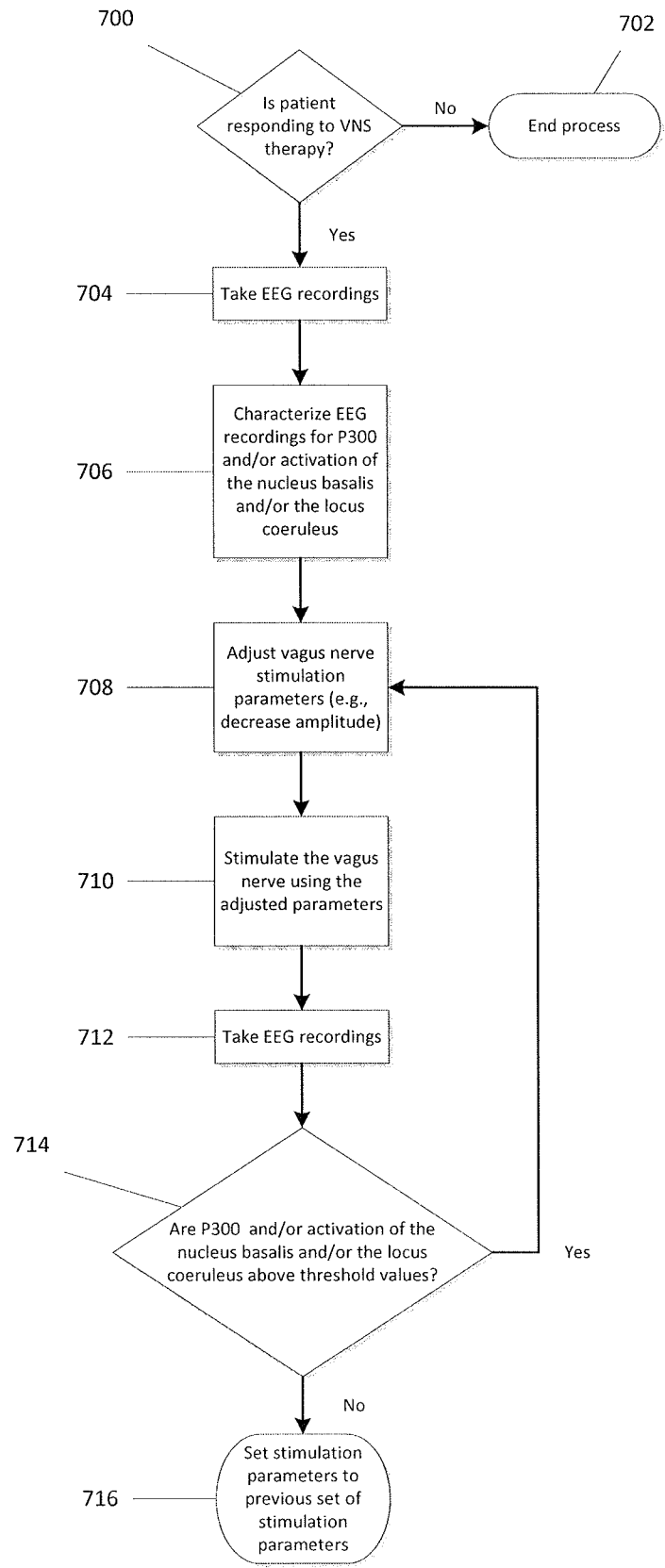
FIG. 7 illustrates a flow chart that describes another method for modulating vagus nerve stimulation using feedback from EEG recordings.

FIG. 7 illustrates a flow chart that describes another method for modulating vagus nerve stimulation using feedback from EEG recordings. This flow chart is particularly suited for reducing the intensity of the VNS treatment in a patient that is responding well to VNS. By reducing the intensity of the VNS treatment, the patient's pain can be reduced and comfort can be improved. In step 700, the patient's response to VNS treatment is determined. If the patient is not responding well to VNS, then this treatment protocol is not suitable and the process ends in step 702. If the patient is responding well to VNS, then the process proceeds to step 704 where EEG recordings are taken. Next, in step 706, the physician or a computing device analyzes and characterizes the EEG recordings for P300 and/or activation of the NB and/or the LC. Then, in step 708, the VNS parameters can be adjusted, by for example, decreasing the amplitude or the duration of the stimulation. In step 710, the vagus nerve is stimulated using the adjusted parameters. In step 712, another set of EEG recordings are taken. In step 714, the EEG recordings can be analyzed and characterized to determine whether P300 and/or activation of the NB and/or LC are present and/or are above thresholds. The thresholds can be predetermined or can be based on the initial characterization of the EEG recordings performed in step 706. If P300 and/or activation of the NB and/or LC is still detected and/or are still above the thresholds, then the process loops back to step 708 wherein the stimulation parameters can be further adjusted, for example, by again decreasing amplitude and/or duration. If in step 714, P300 and/or activation of the NB and/or LC is not detected and/or falls below the threshold, then the stimulation parameters can be set to a previous set of stimulation parameters, as shown in step 716, wherein P300 and/or activation of NB and/or LC were detected and/or above the threshold.

Figure 8:
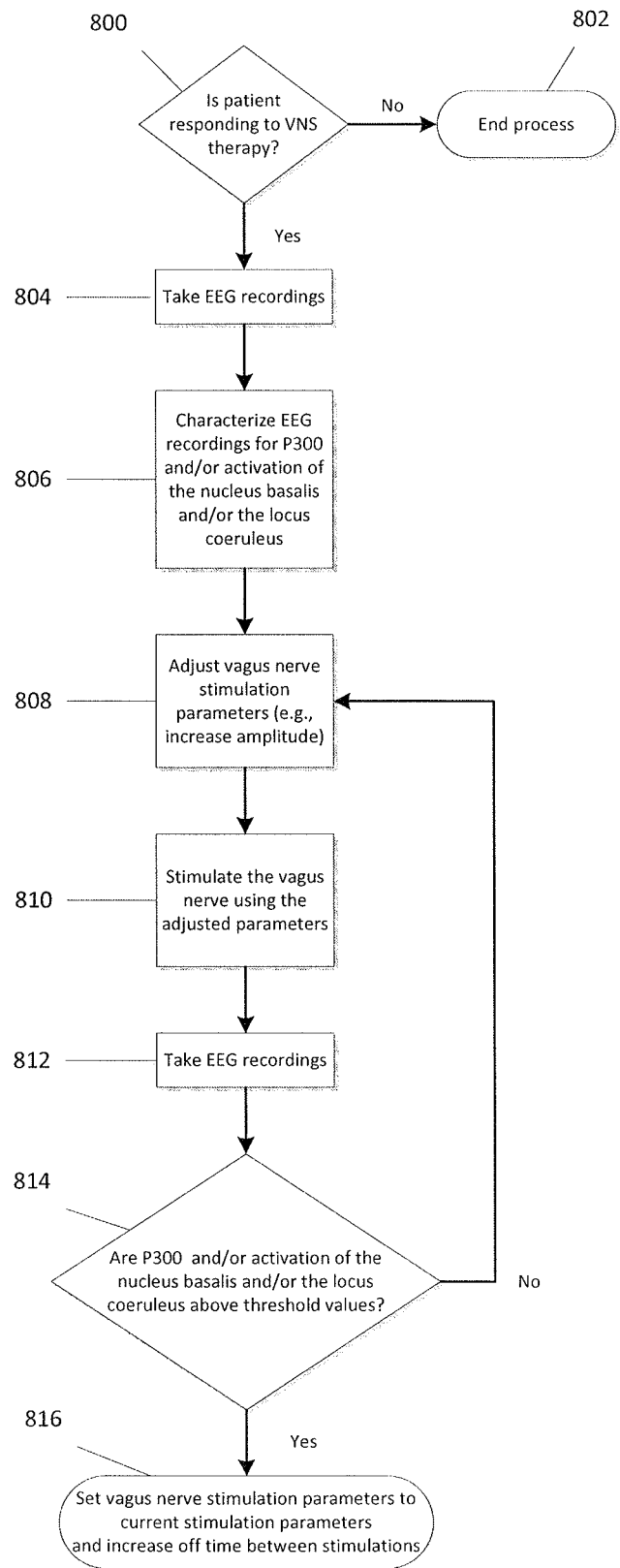
FIG. 8 illustrates a flow chart that describes yet another method for modulating vagus nerve stimulation using feedback from EEG recordings.

FIG. 8 illustrates a flow chart that describes yet another method for modulating vagus nerve stimulation using feedback from EEG recordings. This flow chart is particularly suitable for a patient that is responding well to VNS therapy who wishes to increase the interval between stimulations (the off time). In step 800, the patient is checked to determine whether the patient is responding well to VNS. If not, the process is not suitable and is ended in step 802. If the patient is responding well to VNS, the process proceeds to step 804 where EEG recordings are taken. In step 806, the EEG recordings are analyzed and characterized for P300 and/or activation of the NB and/or LC. In step 808, the vagus nerve stimulation parameters are adjusted by, for example, increasing the amplitude and/or duration. In step 810, the vagus nerve can be stimulated using the adjusted parameters, and EEG recordings can be taken in step 812. In step 814, the EEG recordings are analyzed and characterized to determine whether P300 and/or activation of the NB and/or the LC is detected and/or above threshold values. The threshold values can be predetermined or can be determined based on a comparison with a baseline EEG, such as the EEG recordings taken in step 804 and analyzed and characterized in step 806. If the determination in step 812 is that P300 and/or activation of the NB and/or the LC is not detected and/or falls below the threshold values, then the process loops back to step 808 where the VNS parameters are adjusted by, for example, further increasing the amplitude and/or duration. If the determination in step 812 is that P300 and/or activation of the NB and/or the LC is detected and/or falls above the threshold values, then the VNS parameters can be set to the current stimulation parameters and the off time between stimulations can be increased, as shown in step 816. In some embodiments, the off time can be increased by at least 4, 6, 8, 12, 24, 36, or 48 hours.

Use case example A: A subject with rheumatoid arthritis is not responding to VNS treatment. The physician will record P300 and EEG measurements of activation of the Nucleus Basalis and/or the Locus coeruleus during delivery of test doses. Stimulation dose will increase in intensity, such as amplitude, until change in P300 and activation of the Nucleus Basalis and/or the Locus coeruleus is detected. The physician will then program the applicable stimulation parameters for scheduled dosing.

Use case example B: A subject with rheumatoid arthritis is responding well to once daily VNS treatment. The physician will record P300 and EEG measurements of activation of the Nucleus Basalis and/or the Locus coeruleus during delivery of test doses. Stimulation dose will decrease in intensity, such as amplitude, until change in P300 and activation of the Nucleus Basalis and/or the Locus coeruleus is detected. The physician will then program the applicable stimulation parameters for scheduled dosing.

Use case example C: A subject with rheumatoid arthritis is responding well to once daily VNS treatment. The physician intends to decrease the weekly frequency of stimulation. The physician will record P300 and EEG measurements of activation of the Nucleus Basalis and/or the Locus coeruleus during delivery of test doses. Stimulation dose will increase in intensity, such as amplitude, until change in P300 and activation of the Nucleus Basalis and/or the Locus coeruleus is detected. The physician will then program a greater interval between doses of stimulation.

A closed loop system can include an EEG device, an implantable nerve stimulator (e.g. vagus nerve), a prescription pad and an energizer. The EEG device can measure intracranial potentials and interpret P300, and/or activation of the Nucleus Basalis and/or the Locus coeruleus. The EEG device can communicate through wire or wirelessly, e.g. by Bluetooth protocol, to the prescription pad or energizer which programs stimulation parameters into the implantable nerve stimulator. A controller within the prescription pad, energizer, or EEG device can adjust one or more stimulation parameters, e.g. pulse width, pulse amplitude, pulse frequency, which can be programmed and carried out by the nerve stimulator. For example, the controller can be programmed to increase various stimulation parameters, such as amplitude, until P300 and/or activation of the NB and/or LC is detected by the EEG device. In some embodiments, the controller can be programmed to increase the interval, e.g. the off time, between doses of VNS when P300 and/or activation of the NB and/or LC is detected. In some embodiments, the controller can be programmed to decrease various stimulation parameters, such as amplitude, when P300 and/or activation of the NB and/or LC is detected.

Deep Brain Stimulation and Transcranial Magnetic Stimulation

In some embodiments, deep brain stimulation and/or transcranial magnetic stimulation of Nucleus Basalis and/or the Locus coeruleus can be used to treat chronic inflammatory disease, e.g. rheumatoid arthritis and Crohn's disease. As described above, stimulation of the NB and LC can be used to induce long term potentiation of the inflammatory reflex. In some variations, the deep brain stimulation and trans-cranial magnetic stimulation directly activates the anti-inflammatory reflex. In some embodiments, the deep brain stimulation and/or transcranial magnetic stimulation can be used in conjunction of VNS, while in other embodiments, it can be used without VNS to directly activate the inflammatory reflex through stimulation of the NB and LC. In some embodiments, if used with VNS, the deep brain stimulation and/or transcranial magnetic stimulation can be delivered prior to the VNS to first potentiate the inflammatory reflex before delivering the VNS. In other embodiments, if used with VNS, the deep brain stimulation and/or transcranial magnetic stimulation can be delivered concurrently with the VNS to potentiate the inflammatory reflex while delivering the VNS.

Figure 9:
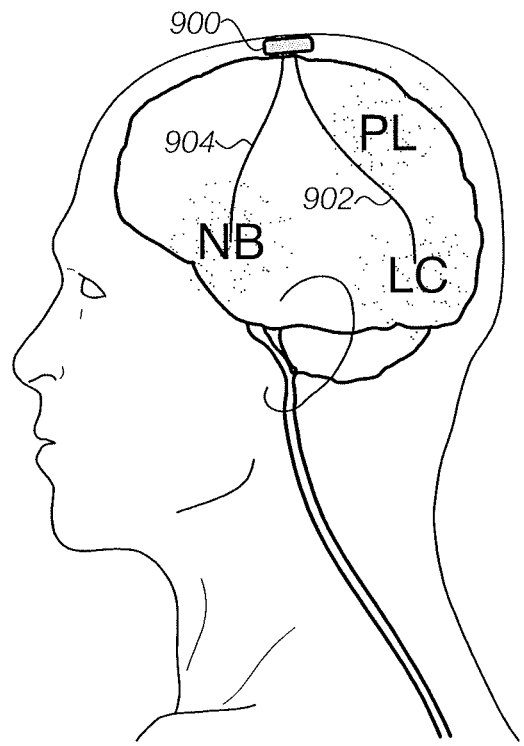
FIG. 9 illustrates an embodiment of a deep brain stimulator with electrodes positioned at the nucleus basalis and locus coeruleus.

FIG. 9 illustrates a deep brain stimulator 900 that can be implanted with electrodes 902, 904 positioned at the NB and/or LC, thereby allowing the stimulator 900 to deliver electrical stimulation to the NB and/or LC. The stimulation can be delivered using stimulation parameters of about 10-10,000 uA, 50-500 Hz for 5-120 minutes per session. Sessions can be given at a frequency of twice/day, once/day, once/two days, once/three days, once/four days, once/five days, once/six days, and once/seven days, once/14 days, and once/month.

Figure 10:
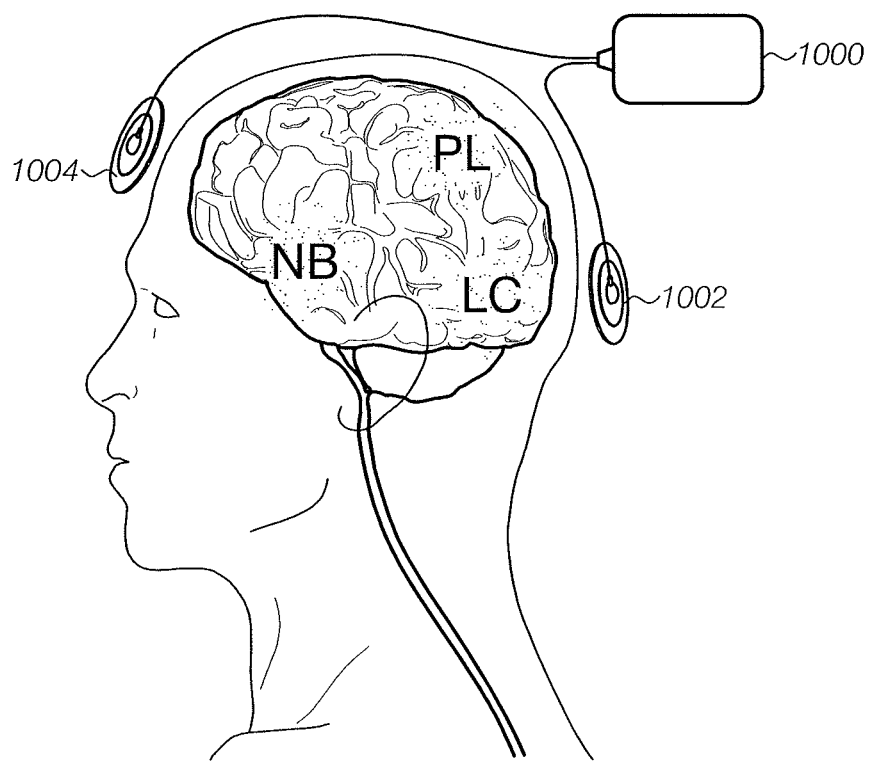
FIG. 10 illustrates an embodiment of a transcranial magnetic stimulator.

In some embodiments, as illustrated in FIG. 10, a transcranial magnetic stimulator 1000 can be used to stimulate the NB and/or LC. The transcranial magnetic stimulator can have one or more coils 1002, 1004 that generate a magnetic field for stimulating the NB and/or LC. The depth of penetration of the magnetic field can be tailored to focus the magnetic field on the NB and/or LC. The stimulation can be provided at either low frequency (<3 Hz) or high frequency (3-25 Hz) for 5 minutes to 120 minutes per session with a magnetic field of up to about 3 Tesla. Sessions can be given at a frequency of twice/day, once/day, once/two days, once/ three days, once/four days, once/five days, once/six days, and once/seven days, once/14 days, and once/month.

Use case example A: At least one electrode is implanted into the Nucleus Basalis and/or the Locus coeruleus of a subject with a chronic inflammatory disease, e.g. rheumatoid arthritis. The brain, specifically the NB and/or LC, is stimulated with electrical current, eg. 10-100 uA, 50-500 Hz for 5 minutes to 1 hr per session.

Use case example B: A trans-cranial magnetic coil is oriented for stimulation into the Nucleus Basalis and/or the Locus coeruleus of a subject with a chronic inflammatory disease, e.g. rheumatoid arthritis. The brain, specifically the NB and/or the LC, is stimulated with at either low frequency (<3 Hz) or high frequency (3-25 Hz) for 5 minutes to 1 hr per session with a magnetic field of up to about 3 Tesla.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. A method of titrating a vagus nerve stimulation dosage of an implanted vagus nerve stimulator for inducing long term potentiation of the inflammatory reflex in a patient, the method comprising:
   stimulating the vagus nerve of the patient according to a dosage of stimulation parameters to stimulate an anti-inflammatory pathway;
   recording an electroencephalogram (EEG) while stimulating the vagus nerve;
   analyzing the recorded EEG to detect activation of at least one of the nucleus basalis and the locus coeruleus indicating stimulation of the anti-inflammatory pathway;
   adjusting the dose of the implanted vagus nerve stimulator, wherein adjusting comprises decreasing one or more of an amplitude, a pulse width, a pulse frequency and a duration of the stimulation parameters if the recorded EEG indicates activation of at least one of the nucleus basalis and the locus coeruleus, further wherein adjusting comprises increasing one or more of the amplitude, the pulse width, the pulse frequency and the duration of the stimulation parameters if the recorded EEG does not indicate activation of at least one of the nucleus basalis and the locus coeruleus; and
   repeating the steps of stimulating, recording, analyzing and adjusting until the dose of the implanted vagus nerve stimulator is at a minimum level necessary to modulate the inflammatory reflex.

2. The method of claim 1, wherein adjusting the dose comprises increasing a current amplitude if the recorded EEG indicates activation.

3. The method of claim 1, further comprising recording a baseline EEG.

4. The method of claim 3, wherein analyzing the recorded EEG to detect activation of at least one of the nucleus basalis and the locus coeruleus by the vagus nerve stimulation comprises comparing the recorded EEG with the baseline EEG.

5. The method of claim 1, wherein adjusting the dose comprises decreasing a time between stimulations if the recorded EEG indicates activation of at least one of the nucleus basalis and the locus coeruleus.

6. The method of claim 1, wherein adjusting the dose comprises increasing a time between stimulations and decreasing a current intensity if the recorded EEG does not indicate activation of at least one of the nucleus basalis and the locus coeruleus.

7. The method of claim 1, wherein analyzing the recorded EEG to detect activation of one or more of the nucleus basalis and the locus coeruleus comprises detecting a P300 signal.

8. The method of claim 1, wherein analyzing the recorded EEG to detect activation of one or more of the nucleus basalis and the locus coeruleus comprises detecting activation of both of the nucleus basalis and the locus coeruleus.

9. A method of titrating a vagus nerve stimulation dosage of an implanted vagus nerve stimulator for inducing long term potentiation of the inflammatory reflex in a patient, the method comprising:
   recording a baseline electroencephalogram (EEG) before stimulating the vagus nerve to stimulate an anti-inflammatory pathway;
   recording a second EEG while stimulating the vagus nerve with a dose of vagus nerve stimulation;
   determining from the baseline EEG and the second EEG if at least one of the nucleus basalis and the locus coeruleus has been activated indicating that the anti-inflammatory pathway has been stimulated by the vagus nerve stimulation; and
   adjusting the dose of the implanted vagus nerve stimulator, wherein adjusting comprises decreasing one or more of an amplitude, pulse width, pulse frequency and duration of stimulation parameters if at least one of the nucleus basalis and the locus coeruleus has been activated, wherein adjusting comprises increasing one or more of the amplitude, pulse width, pulse frequency and duration of the stimulation parameters if at least one of the nucleus basalis and the locus coeruleus has not been activated; and
   repeating the steps of recording the second EEG, determining and adjusting until the dosage of the implanted vagus nerve stimulator is at a minimum level necessary to modulate the inflammatory reflex.

10. The method of claim 9, wherein the stimulation parameters are adjusted between an amplitude of between 0.1 and 3 mA, a frequency of between 1 Hz and 30 Hz, a pulse width of between 100 microseconds and 500 microseconds, and a duration of between about 0.5 second to 10 minutes.

11. The method of claim 9, further comprising waiting an off time between the stimulation and re-stimulation of greater than two hours when repeating the steps of recording the second EEG, determining and adjusting.

12. The method of claim 9, wherein the stimulation is sufficient to modulate cytokine release when at least one of the nucleus basalis and the locus coeruleus have been activated.

13. The method of claim 9, wherein determining from the baseline EEG and the second EEG if at least one of the nucleus basalis and the locus coeruleus has been activated comprises detecting a P300 signal.

14. The method of claim 9, wherein determining from the baseline EEG and the second EEG if at least one of the nucleus basalis and the locus coeruleus has been activated comprises determining from the baseline EEG and the second EEG that both of the nucleus basalis and the locus coeruleus have been activated.

\* \* \* \* \*